(12) United States Patent
Suetoshi et al.

(10) Patent No.: US 8,372,007 B2
(45) Date of Patent: Feb. 12, 2013

(54) METHOD AND DEVICE OF DETECTING SHAPE AND BONE STRENGTH DIAGNOSTIC DEVICE USING THE DEVICE

(75) Inventors: Ryoichi Suetoshi, Nishinomiya (JP); Atsushi Uodome, Nishinomiya (JP); Dorian Cretin, Nishinomiya (JP)

(73) Assignee: Furuno Electric Co., Ltd., Nishinomiya (JP)

( * ) Notice: Subject to any disclaimer, the term of this patent is extended or adjusted under 35 U.S.C. 154(b) by 520 days.

(21) Appl. No.: 12/508,974

(22) Filed: Jul. 24, 2009

(65) Prior Publication Data

US 2010/0018313 A1    Jan. 28, 2010

(30) Foreign Application Priority Data

Jul. 25, 2008  (JP) .................. 2008-191695

(51) Int. Cl.
*A61B 8/00* (2006.01)
(52) U.S. Cl. ..................................... 600/438
(58) Field of Classification Search .................. 600/438
See application file for complete search history.

(56) References Cited

U.S. PATENT DOCUMENTS 3,723,952 A    3/1973    Walsh

FOREIGN PATENT DOCUMENTS

| DE | 1265004 B | 3/1968 |
|---|---|---|
| DE | 2914771 A1 | 10/1979 |
| GB | 2018992 A | 10/1979 |
| JP | 62-121354 A | 6/1987 |
| JP | 04-317641 A | 11/1992 |
| JP | 2002-131426 A | 5/2002 |
| WO | WO-85/05694 A1 | 12/1985 |
| WO | WO-99/45348 A1 | 9/1999 |
| WO | WO-03/099132 A1 | 12/2003 |
| WO | WO-03/099133 A1 | 12/2003 |

*Primary Examiner* — Jonathan Cwern
(74) *Attorney, Agent, or Firm* — Birch, Stewart, Kolasch & Birch, LLP

(57) ABSTRACT

A shape detection method and device for detecting a shape of an object are disclosed. The device includes an ultrasonic wave transmission module, a reception module, an incoming direction detecting module, a propagation time detecting module, a front-surface reflection point detecting module, and a shape deriving module. The shape deriving module derives a shape of a front surface of the object using a plurality of the reflection points on the front surface of the object detected by the front-surface reflection point detecting module for a plurality of transducer groups.

11 Claims, 23 Drawing Sheets

METHOD AND DEVICE OF DETECTING SHAPE AND BONE STRENGTH DIAGNOSTIC DEVICE USING THE DEVICE

CROSS-REFERENCE TO RELATED APPLICATION(S)

This application claims priority under 35 U.S.C. §119 to Japanese Patent Application No. 2008-191695, which was filed on Jul. 25, 2008, the entire disclosure of which is hereby incorporated by reference.

TECHNICAL FIELD

The present invention relates to a shape detection method and a shape detection device for detecting a shape of a target object using an ultrasonic wave, and a bone strength diagnostic device using the shape detection device.

BACKGROUND

Conventionally, the following device provided with a plurality of transducers arranged in a single row are well known as a device for detecting a shape of a target object using an ultrasonic wave (for example, refer to JP1992-317641(A)). This conventional shape detection device transmits ultrasonic waves to a target object with the plurality of transducers sequentially from one end of the transducer row, and the same transducer receives a reflected wave from the surface of a target object. Because the distance from each transducer to the front surface of the target object differs, time after an ultrasonic wave is transmitted from each transducer until each transducer receives a reflected wave also differs. Thus, by using the difference in phase of the received wave signals of the reflected waves by the plurality of transducers (i.e., the difference in propagation time from wave transmission to wave reception), the shape of the target object can be detected.

Generally, a transducer is connected with a transmission circuit, and by receiving an electric signal from the transmission circuit, microscopically oscillates to generate an ultrasonic wave. In order to actuate the plurality of transducers in order, it is necessary to sequentially shift the transmission timing of an electric signal for each transducer from the previous one. Therefore, a wave-transmission module of the conventional shape detection device described above needs to be including a plurality of transmission circuits connected to the plurality of transducers, or including a change-over circuit for changing-over the transducer to be connected to the transmission circuit among the plurality of transducers. Therefore, the circuit configuration will be complicated and its cost will increase.

Further, because the conventional shape detection device described above drives the plurality of transducers in order and receives the reflected waves, it requires a certain amount of time for all the transducers to finish the wave transmission and wave reception of ultrasonic waves. Therefore, for example, if the object to be measured is a bone of a living body, the examinee may move while the measurement to lower the detection accuracy.

SUMMARY

Thus, the present invention is made in accordance with the above conditions, and provides a shape detection device with a simple configuration for transmitting an ultrasonic wave and a shortened measuring time, and also provides a shape detecting method and a bone strength diagnostic device using the shape detection device.

According to an aspect of the invention, a shape detection device includes a wave-transmission module for transmitting an ultrasonic wave from a wave-transmission transducer to a target object, a wave-reception module for receiving with a plurality of wave-reception transducers front-surface reflected waves of the ultrasonic wave transmitted from the wave-transmission module on a front surface of the target object, an incoming direction detecting module for detecting an incoming direction of the front-surface reflected wave to each of a plurality of transducer groups using a time difference between timings at which two wave-reception transducers constituting each transducer group receive the front-surface reflected wave, each transducer group being constituted with two wave-reception transducers adjacent to each other among the plurality of wave-reception transducers, a propagation time detecting module for detecting a propagation time of the front-surface reflected wave that reaches each transducer group using a received wave signal of the front-surface reflected wave of at least one of the two wave-reception transducers constituting each transducer group, a front-surface reflection point detecting module for detecting a reflection point of the ultrasonic wave on the front surface of the target object based on the incoming direction and the propagation time of the front-surface reflected wave detected for each transducer group by the incoming direction detecting module and the propagation time detecting module, respectively, and a shape deriving module for deriving a shape of the front surface of the target object using a plurality of the reflection points on the front surface of the target object detected by the front-surface reflection point detecting module for a plurality of the transducer groups.

The ultrasonic wave transmitted from one wave-transmission transducer is reflected on the surface of the target object, and the resulting front-surface reflected waves are received by the plurality of wave-reception transducers. The incoming direction and the propagation time of the front-surface reflected wave that reaches each transducer group constituted with the two wave-reception transducers adjacent to each other among the plurality of wave-reception transducers are detected, and the reflection points on the surface of the target object are detected using these values. Because the propagating direction of the ultrasonic wave transmitted from one wave-transmission transducer is known beforehand, the reflection point can be detected by using the incoming direction and the propagation time which are detected, even if from which position of the wave-transmission transducer the front-surface reflected wave is transmitted is not identified. Similarly for other transducer groups, by detecting the reflection points on the surface of the target object, a plurality of reflection points can be detected and, thus, the shape of the front surface of the target object can be derived.

Further, because the ultrasonic wave is transmitted from one wave-transmission transducer, the configuration of the wave-transmission module can be simple. Further, because the ultrasonic wave is transmitted from one wave-transmission transducer and the reflected waves are received, a measuring time can be shortened compared with the case where ultrasonic waves are transmitted from a plurality of wave-transmission transducers, wave transmission timings of which are shifted from each other, and a plurality of reflected waves produced by this are received.

The wave-transmission transducer may serve as the wave-reception transducer as well.

The wave-transmission transducer and the plurality of wave-reception transducers may be arranged in a single row.

The wave-transmission transducer and the plurality of wave-reception transducers may be arranged in a matrix.

The wave-transmission transducer may include a plurality of wave-transmission transducers for simultaneously transmitting ultrasonic waves.

The ultrasonic waves simultaneously transmitted from the plurality of wave-transmission transducers propagate as a plane wave and are reflected on the front surface of the target object, and the front-surface reflected waves produced by this are received by the plurality of wave-reception transducers. In this case, it is not determined that the front-surface reflected wave received by each wave-reception transducer is transmitted from which wave-transmission transducer. Thus, the incoming direction and the propagation time of the front-surface reflected wave that reaches each transducer group constituted with the two wave-reception transducers adjacent to each other among the plurality of wave-reception transducers are detected, and the reflection points on the front surface of the target object are detected using these values. Because the propagating direction of the ultrasonic wave (plane wave) transmitted from the plurality of wave-transmission transducers is known beforehand, the reflection point can be detected by using the incoming direction and the propagation time which are detected, even if from which wave-transmission transducer the front-surface reflected wave is transmitted is not identified. Similarly for other transducer groups, by detecting the reflection points on the front surface of the target object, a plurality of reflection points are detected and a shape of the front surface of the target object can be derived.

In order to transmit the ultrasonic waves simultaneously from the plurality of wave-transmission transducers, the same electric signal (transmitted wave signal) may be simply transmitted to the plurality of wave-transmission transducers. Therefore, the configuration of the wave-transmission module can be simplified compared with the case where wave transmission timings of the plurality of wave-transmission transducers are shifted from each other to transmit the ultrasonic waves (that is, electric signals are sent to the plurality of wave-transmission transducers while being shifted their timings).

Further, because the ultrasonic waves are simultaneously transmitted from the plurality of wave-transmission transducers and the reflected waves are received, a measuring time can be shortened compared with the case where ultrasonic waves are transmitted from the plurality of wave-transmission transducers while wave transmission timings are shifted and a plurality of reflected waves produced by this are received.

The center frequency of the ultrasonic wave transmitted from the wave-transmission transducer may be 1 to 10 MHz, and a length in the arranged direction of the wave-transmission transducer may be 10 to 100 mm.

The wave-reception module may receive back-surface reflected waves on a back surface of the target object that reach the plurality of wave-reception transducers after the front-surface reflected waves. The incoming direction detecting module may detect an incoming direction of the back-surface reflected wave to each of a plurality of transducer groups using a time difference between timings at which the two wave-reception transducers constituting each transducer group receive the back-surface reflected waves. The propagation time detecting module may detect a propagation time of the back-surface reflected wave that reaches each transducer group using a received wave signal of the back-surface reflected wave of at least one of the two wave-reception transducers constituting each transducer group. The shape detection device may further include a back-surface reflection point detecting module for detecting a reflection point of the ultrasonic wave on the back surface of the target object based on the incoming direction and the propagation time of the back-surface reflected wave detected for each transducer group by the incoming direction detecting module and the propagation time detecting module, respectively, and the shape of the front surface of the target object derived by the shape deriving module. The shape deriving module may derive a shape of the back surface of the target object using a plurality of the reflection points on the back surface of the target object detected by the back-surface reflection point detecting module for a plurality of the transducer groups.

According to another aspect of the invention, a bone strength diagnostic device using the shape detection device described above where the target object is a bone. The shape deriving module may derive a thickness of the bone based on the derived shapes of the front surface and the back surface of the bone. The bone strength diagnostic device may include a bone strength diagnostic module for diagnosing a bone strength based on the thickness of the bone.

According to this configuration, the bone thickness can be derived by transmitting the ultrasonic wave to a bone, receiving the reflected wave from the bone front surface and the bone back surface, and using the received wave signals. Because the bone thickness is one of the factors to determine the bone strength, the device can diagnose the bone strength from the bone thickness.

According to still another aspect of the invention, a shape detection device includes a wave-transmission module for simultaneously transmitting ultrasonic waves from a plurality of wave-transmission transducers to a target object having a plurality of layers, a wave-reception module for receiving, with a plurality of wave-reception transducers, reflected waves of the ultrasonic wave transmitted from the wave-transmission module on a front surface of the target object and a back surface of each layer of the target object, an incoming direction detecting module for detecting incoming directions of the reflected waves on the front surface of the target object and the back surface of each layer to each of a plurality of transducer groups using a time difference between received wave signals of two wave-reception transducers constituting each transducer group, each transducer group being constituted with two wave-reception transducers adjacent to each other among the plurality of wave-reception transducers, a propagation time detecting module for detecting a propagation time of each of the reflected waves that reaches each transducer group using the received wave signal of each reflected wave of at least one of the two wave-reception transducers constituting each transducer group, an outermost-layer front-surface shape detecting module for detecting a reflection point of the ultrasonic wave on the front surface of the target object to derive a shape of the front surface of the target object based on the incoming direction and the propagation time of the reflected wave from the front surface of the target object detected for each transducer group by the incoming direction detecting module and the propagation time detecting module, and a back-surface shape deriving module for deriving a shape of the back surface of each layer sequentially from the outermost layer of the target object based on the incoming direction and the propagation time of the reflected wave from the back surface of each layer detected for each transducer group by the incoming direction detecting module and the propagation time detecting module, and the shape of the front surface of the target object detected by the outermost-layer front-surface shape detecting module.

The ultrasonic waves simultaneously transmitted from the plurality of wave-transmission transducers propagate as a plane wave, and some of the ultrasonic waves are reflected on the front surface of the target object (front surface of the outermost layer), the remaining ultrasonic waves passed through the outermost layer reflect on the back surface of each layer sequentially from the outermost layer of the target object. The resulting plurality of reflected waves are received by the plurality of transducers. The incoming direction and the propagation time of each reflected wave that reaches each transducer group constituted with two wave-reception transducers adjacent to each other among the plurality of wave-reception transducers are detected. Using the incoming directions and the propagation times of the reflected waves from the front surface of the target object that reach each transducer group, a plurality of reflection points on the front surface of the target object are detected to detect the shape of the front surface of the target object. Further, the shape of the back surface of each layer is detected sequentially from the outermost layer of the target object using the incoming directions of the reflected waves from the back surface of each layer of the target object that reaches each transducer group, and the shape of the front surface of the target object detected in advance. Thus, the shape of the target object having a plurality of layers can be detected by detecting the shape of each layer sequentially from the outermost layer of the target object.

In order to transmit the ultrasonic waves simultaneously from the plurality of wave-transmission transducers, the same electric signal (transmitted wave signal) may be simply transmitted to the plurality of wave-transmission transducers. Therefore, the configuration of the wave-transmission module can be simplified compared with the case where wave transmission timings of the plurality of wave-transmission transducers are shifted from each other to transmit the ultrasonic waves (that is, electric signals are sent to the plurality of wave-transmission transducers while being shifted their timings).

The wave-transmission transducer may include a plurality of wave-transmission transducers. The incoming direction detecting module may detect an incoming direction of the front-surface reflected waves using a first time difference between wave-reception timings of first two wave-reception transducers and a second time difference between wave-reception timings of second two wave-reception transducers, where the first and second wave-reception transducers are constituted with three or four wave-reception transducers selected from the plurality of wave-reception transducers and are arranged in two intersecting rows. The three or four wave-reception transducers may be proximate to each other to constitute each transducer group. The incoming direction detecting module may further detect an incoming direction of the front-surface reflected waves to each transducer group based on the first incoming direction and the second incoming direction. The propagation time detecting module may detect a propagation time of the front-surface reflected wave that reaches each transducer group using a received wave signal of the front-surface reflected wave of at least one of the three or four wave-reception transducers constituting each transducer group.

According to this configuration, even if the shape of the front surface of the target object is a three-dimensional shape, such as a spherical shape, the shape can be detected three-dimensionally.

According to another aspect of the invention, a shape detection method includes simultaneously transmitting ultrasonic waves from a plurality of wave-transmission transducers to a target object, receiving with a plurality of wave-reception transducers front-surface reflected waves of the transmitted ultrasonic wave on a front surface of the target object, detecting an incoming direction of the front-surface reflected wave to each of a plurality of transducer groups using a time difference between timings at which two wave-reception transducers constituting each transducer group receive the front-surface reflected waves, each transducer group being constituted with two wave-reception transducers adjacent to each other among the plurality of wave-reception transducers, detecting a propagation time of the front-surface reflected wave that reaches each transducer group using a received wave signal of the front-surface reflected wave of at least one of the two wave-reception transducers constituting each transducer group, detecting a reflection point of the ultrasonic wave on the front surface of the target object based on the incoming direction and the propagation time of the front-surface reflected wave detected for each transducer group, and deriving a shape of the front surface of the target object using a plurality of the reflection points on the front surface of the target object detected for a plurality of the transducer groups.

The ultrasonic waves simultaneously transmitted from the plurality of wave-transmission transducers propagate as a plane wave and are reflected on the front surface of the target object, and the front-surface reflected waves produced by this are received by the plurality of wave-reception transducers. In this case, it is not determined that the front-surface reflected wave received by each wave-reception transducer is transmitted from which wave-transmission transducer. Thus, the incoming direction and the propagation time of the front-surface reflected wave that reaches each transducer group constituted with the two wave-reception transducers adjacent to each other among the plurality of wave-reception transducers are detected, and the reflection points on the front surface of the target object are detected using these values. Because the propagating direction of the ultrasonic wave (plane wave) transmitted from the plurality of wave-transmission transducers is known beforehand, the reflection point can be detected by using the incoming direction and the propagation time which are detected, even if from which wave-transmission transducer the front-surface reflected wave is transmitted is not identified. Similarly for other transducer groups, by detecting the reflection points on the front surface of the target object, a plurality of reflection points are detected and a shape of the front surface of the target object can be derived.

In order to transmit the ultrasonic waves simultaneously from the plurality of wave-transmission transducers, the same electric signal (transmitted wave signal) may be simply transmitted to the plurality of wave-transmission transducers. Therefore, the configuration of the wave-transmission module can be simplified compared with the case where wave transmission timings of the plurality of wave-transmission transducers are shifted from each other to transmit the ultrasonic waves (that is, electric signals are sent to the plurality of wave-transmission transducers while being shifted their timings).

Further, because the ultrasonic waves are simultaneously transmitted from the plurality of wave-transmission transducers and the reflected waves are received, a measuring time can be shortened compared with the case where ultrasonic waves are transmitted from the plurality of wave-transmission transducers while wave transmission timings are shifted and a plurality of reflected waves produced by this are received.

The receiving front-surface reflected waves may include receiving back-surface reflected waves on a back surface of the target object that reach the plurality of wave-reception transducers after the front-surface reflected waves. The detecting the incoming direction of the front-surface reflected wave may include detecting an incoming direction of the back-surface reflected wave to each transducer group using a time difference between timings at which the two wave-reception transducers constituting each transducer group receive the back-surface reflected wave. The detecting the propagation time of the front-surface reflected wave may include detecting a propagation time of the back-surface reflected wave that reaches each transducer group using a received wave signal of the back-surface reflected wave of at least one of the two wave-reception transducers constituting each transducer group. The method may further include detecting a reflection point of the ultrasonic wave on the back surface of the target object based on the incoming direction and the propagation time of the back-surface reflected wave detected for each transducer group, and the derived shape of the front surface of the target object. The deriving the shape of the front surface may include deriving a shape of the back surface of the target object using a plurality of the reflection points on the back surface of the target object detected for the plurality of transducer groups.

BRIEF DESCRIPTION OF THE DRAWINGS

The present disclosure is illustrated by way of example and not by way of limitation in the figures of the accompanying drawings, in which the like reference numerals indicate like elements and in which:

FIG. 15A shows an arrayed transducer of Modified Embodiment 7, FIG. 15B shows an arrayed transducer of Modified Embodiment 8, and FIG. 15C shows an ultrasonic transceiver having an arrayed transducer of Modified Embodiment 9 added with a change-over circuit;

FIG. 16A shows an ultrasonic transceiver of Modified Embodiment 12, FIG. 16B shows an ultrasonic transceiver of Modified Embodiment 13, and FIG. 16C shows an ultrasonic transceiver of Modified Embodiment 14;

FIG. 19A shows transducers of Modified Embodiment 18 and Modified Embodiment 19, FIG. 19B is a schematic view for illustrating a method of detecting an incoming direction of reflected waves according to Modified Embodiment 18, and FIG. 19C is a schematic view for illustrating a method of detecting an incoming direction of reflected waves according to Modified Embodiment 19.

DETAILED DESCRIPTION

Hereinafter, embodiments of the present invention is explained with reference to the appended drawings.

In this embodiment, an example in which a shape detection device according to the invention is applied to a part of a bone strength diagnostic device 1 will be particularly described without limiting the claims. The bone strength diagnostic device 1 of this embodiment detects a bone shape and derives a speed of sound of an ultrasonic wave that propagates along the bone surface using the detected bone shape to diagnose bone strength.

The bone strength diagnostic device 1 diagnoses a bone inside a body such as, but not limited to, a cortical bone of long-pipe shape, such as a tibia, for example. Typically, a bone is configured with a cortical bone and a cancellous bone of a shape of meshes which exists inside the cortical bone.

Figure 1:
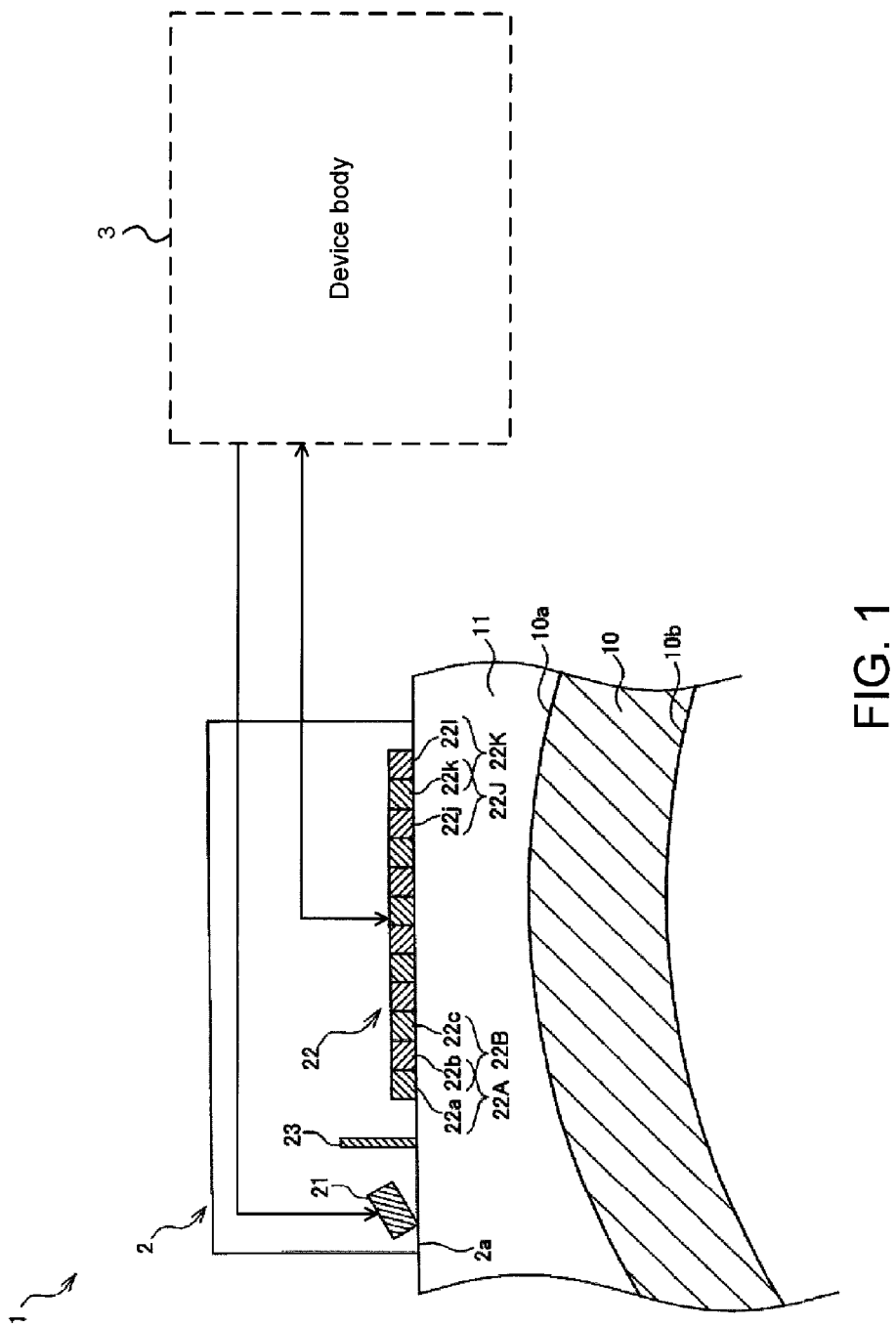
FIGS. 1 and 1B are a schematic diagram showing a configuration of a bone strength diagnostic device according to an embodiment of the present invention.

As shown in FIG. 1, a surface $10a$ of a cortical bone 10 (hereinafter, simply referred to as a "bone" in this embodiment) is covered with soft tissues 11, such as muscles and fat. FIG. 1 shows a cross-section perpendicular to the longitudinal direction of the bone 10 (i.e., transverse cross-section), and a shape of the bone front surface $10a$ is formed in a loosely curved surface which is convex toward the side of the soft tissues 11. In this embodiment, although illustration is omitted, the surface of the longitudinal cross-section of the bone 10 may be substantially flat and may be inclined with respect to the surface of the soft tissues 11.

The bone strength diagnostic device 1 of this embodiment derives a speed of sound of an ultrasonic wave propagating along the bone front surface $10a$ in the circumferential direction (hereinafter, referred to as a "circumferential speed of sound") and a speed of sound of an ultrasonic wave propagating along the bone front surface 10a in the longitudinal direction (hereinafter, referred to as a "longitudinal speed of sound"), and then diagnoses a strength of the bone using the speeds of sound of these two directions.

Figure 1B:
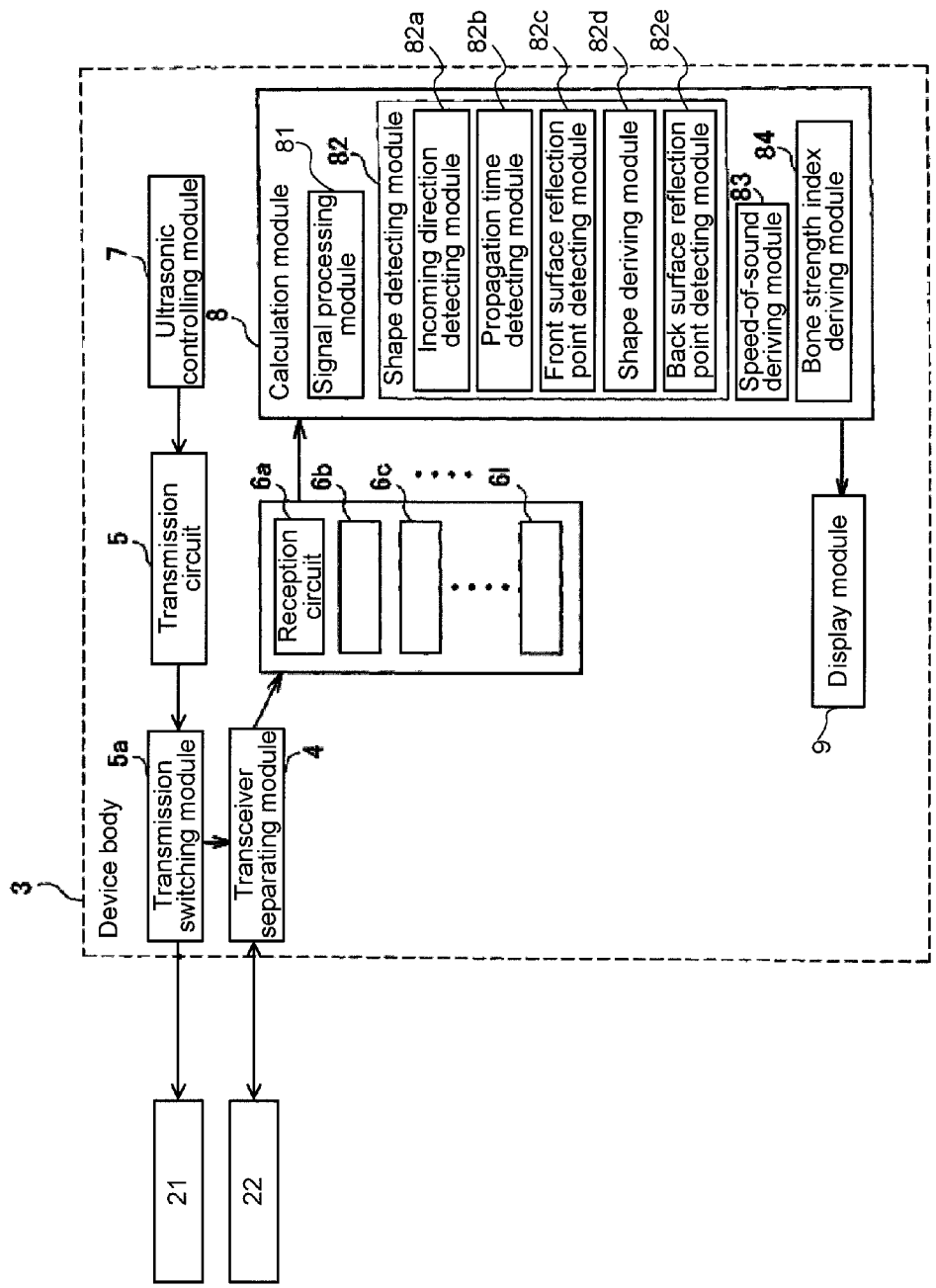

As shown in FIG. 1, the bone strength diagnostic device 1 of this embodiment includes an ultrasonic transceiver 2 and a device body 3. The device body 3 includes, as shown in FIG. 1B, a transceiver separating module 4, a transmission circuit 5, a transmission switching module 5a, a plurality of reception circuits 6a-6l, an ultrasonic controlling module 7, a calculation module 8, and a display module 9.

The ultrasonic transceiver 2 transmits and receives an ultrasonic wave, and is contacted with a surface of the soft tissues 11. The surface of the transducer 2 contacted with the surface of the soft tissues 11 is called herein a "contacting face 2a." The ultrasonic transceiver 2 includes a transducer 21 dedicated to wave transmission, an arrayed transducer 22 having a plurality of transducers 22a-22l (twelve transducers in this embodiment) arranged in a single row, and a sound insulating material 23. The transducer used herein is such that it oscillates when an electric signal is applied to generate an ultrasonic wave from its surface (oscillating surface), and on the other hand, it generates an electric signal when it receives an ultrasonic wave on its surface to be oscillated.

The transducer 21 dedicated to wave transmission, the sound insulating material 23, and the arrayed transducer 22 are aligned in the arrayed direction of the arrayed transducer 22. When measuring the circumferential speed of sound, as shown in FIG. 1, the bone ultrasonic wave transceiver 2 is contacted with the soft tissues 11 so that the arrayed direction of the arrayed transducer 22 is oriented substantially in the circumferential direction of the bone 10. On the other hand, when measuring the longitudinal speed of sound, the ultrasonic transceiver 2 is contacted the soft tissues 11 so that the arrayed direction of the arrayed transducer 22 is oriented substantially in the longitudinal direction of the bone 10.

The transducer 21 dedicated to wave transmission is provided so that its surface (oscillating surface) inclines to the contacting face 2a. As the transducer 21 dedicated to wave transmission, what transmits an ultrasonic wave with a wide directivity may be used (in other words, what has a wide angle range of emitting an ultrasonic wave). The smaller the area of the oscillating surface, the wider the directivity becomes. That is, because sensitivity for the ultrasonic wave and the directivity have a trade-off relation, the installation angle of the transducer 21 dedicated to wave transmission and the dimension of the oscillating surface are designed suitable for an object to be measured.

The twelve transducers 22a-22l that constitute the arrayed transducer 22 are arranged so that their surfaces (oscillating surface) are parallel to the contacting face 2a. Note that, although the number of transducers that constitute the arrayed transducer 22 is twelve in this embodiment, it may be any arbitrary number other than twelve. A horizontal length of the arrayed transducer 22 in the case of FIG. 1 may be 24 mm, for example.

In this embodiment, the sound insulating material 23 is formed in a plate shape and is arranged between the transducer 21 dedicated to wave transmission and the arrayed transducer 22. The material of the sound insulating material 23 may be a material having a sound absorbing function, such as cork, a synthetic rubber, a porous material (for example, a foamed resin material), etc. The sound insulating material 23 prevents the ultrasonic wave transmitted from the transducer 21 dedicated to wave transmission from propagating inside of the ultrasonic transceiver 2 to directly reach the arrayed transducer 22. In other words, it can prevent that an ultrasonic wave unnecessary for deriving a speed of sound in the bone is received by the arrayed transducer 22.

Note that a coupling material (not illustrated) intervenes between the contacting face 2a and the surface of the soft tissues 11. The coupling material prevents a gap from being produced between the contacting face 2a and the surface of the soft tissues 11. In addition, the coupling material adjusts acoustic impedances of the transducers 22a-22l and the soft tissues 11 to suppress the ultrasonic wave transmitted from the transducer 21 dedicated to wave transmission or the arrayed transducer 22 reflecting on the surface of the soft tissues 11.

The transducer 21 dedicated to wave transmission is connected to the transmission circuit 5 via the transmission switching module 5a. The plurality of transducers 22a-22l are connected to the transmission circuit 5 via the transceiver separating module 4 and the transmission switching module 5a. The transmission circuit 5 generates an electric pulse signal to transmit it to the transmission switching module. Note that a chirp signal may be used instead of the electric pulse signal. The center frequency of the electric pulse oscillation may be approximately 1 to 10 MHz, for example.

The transmission switching module 5a transmits the electric pulse signal transmitted from the transmission circuit 5 to any of the transducers 21 dedicated to wave transmission and the arrayed transducer 22. The transmission switching module 5a changes over the transducers to select one that transmits an ultrasonic wave.

The twelve transducers 22a-22l that constitute the arrayed transducer 22 are connected to twelve reception circuits 6a-6l via the transceiver separating module 4, respectively. The reception circuits 6a-6l perform a process, such as an amplifying process, a filtering process, a digital conversion process, to the electric signal transmitted from the transducers 22a-22l, respectively (received wave signal), and then transmit it to the calculation module 8.

The transceiver separating module 4 prevents the transmitted wave signal sent to the arrayed transducer 22 from the transmission circuit 5 (electric pulse signal) from flowing into the reception circuits 6a-6l directly, and prevents the received wave signal sent to the reception circuits 6a-6l from the arrayed transducer 22 from flowing into the transmission circuit 5.

The ultrasonic controlling module 7 is connected with the transmission circuit 5 and transmits a signal for transmitting ultrasonic waves from the twelve transducers 22a-22l to the transmission circuit 5.

Note that the wave-transmission transducers and the wave-reception transducers of the shape detection device in the claims correspond to the twelve transducers 22a-22l that constitute the arrayed transducer 22 in this embodiment. In other words, the wave-transmission transducers serve also as the wave-reception transducers in this embodiment. Therefore, the total number of transducers that receive the ultrasonic waves can be reduced.

Further, the wave-transmission module of the shape detection device in the claims is constituted with the arrayed transducer 22 and the transmission circuit 5 in this embodiment, and the wave-reception module of the shape detection device in the claims is constituted with the arrayed transducer 22 and the twelve reception circuits 6a-6l in this embodiment.

Hereinafter, an operation of the ultrasonic transceiver 2 will be explained.

When Ultrasonic Wave is Transmitted from Arrayed Transducer 22

Figure 2A:
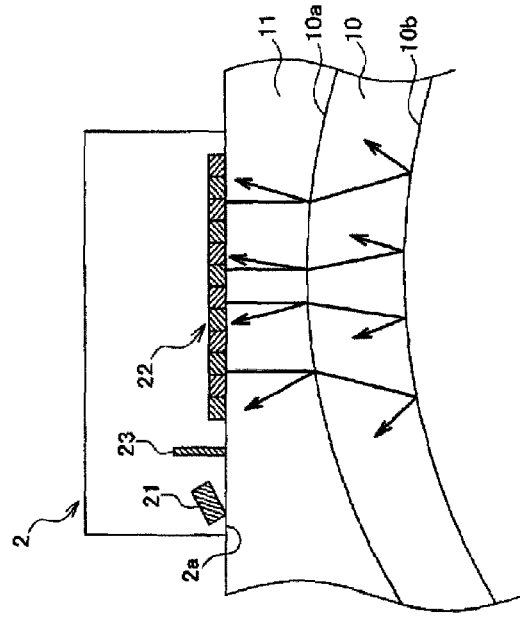
FIG. 2A is a schematic view for illustrating an ultrasonic wave transmitted from an arrayed transducer.

When the arrayed transducer 22 is determined by the transmission switching module 5a to be a transducer that transmits an ultrasonic wave, an electric pulse signal is sent from the transmission circuit 5 to the arrayed transducer 22. The transducers 22a-22l that constitute the arrayed transducer 22 transmit the ultrasonic waves of the same phase to the bone 10 simultaneously (incident wave). As shown in FIG. 2A, the incident waves transmitted from the arrayed transducer 22 propagate inside of the soft tissues 11 as a plane wave. This plane wave travels in a direction perpendicular to the contacting face 2a.

Figure 2B:
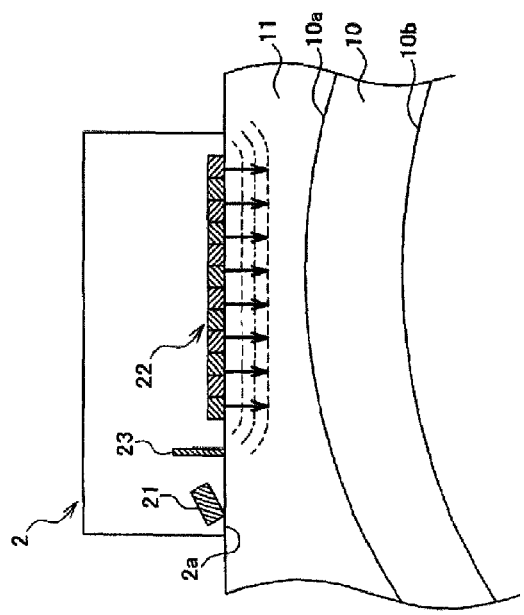
FIG. 2B is a schematic view for illustrating propagation courses of the ultrasonic wave transmitted from the arrayed transducer.

As shown in FIG. 2B, a part of the incident wave is reflected on the bone front surface 10a. A front-surface reflected wave produced by this is received by the transducers 22a-22l. On the other hand, another part of the incident wave that propagates inside of the bone 10 without reflecting on the bone front surface 10a is reflected on the back surface 10b of the bone 10. The back-surface reflected wave produced by this is received by the transducers 22a-22l after the front-surface reflected wave. Therefore, the front-surface reflected wave or the back-surface reflected wave received by each of the transducers 22a-22l may not be determined from which transducer transmitted.

Preferably, a spatial relationship from the arrayed transducer 22 to the bone front surface 10a may be a short-distance field such that the plane wave transmitted from the arrayed transducer 22 propagates to the bone front surface 10a without being spread. Thus, an accuracy of detecting the shape of the bone front surface 10a can be improved. Preferably, the distance from the arrayed transducer 22 to the bone back surface 10b may also be close.

When the transducers 22a-22l receive the front-surface reflected wave or the back-surface reflected wave, they convert the acoustic wave into an electric signal, and then transmit the electric signal (received wave signal) to the reception circuits 6a-6l via the transceiver separating module 4, respectively. Thus, the wave reception of the front-surface reflected wave and the back-surface reflected wave is performed independently by the transducers 22a-22l.

Figure 3:
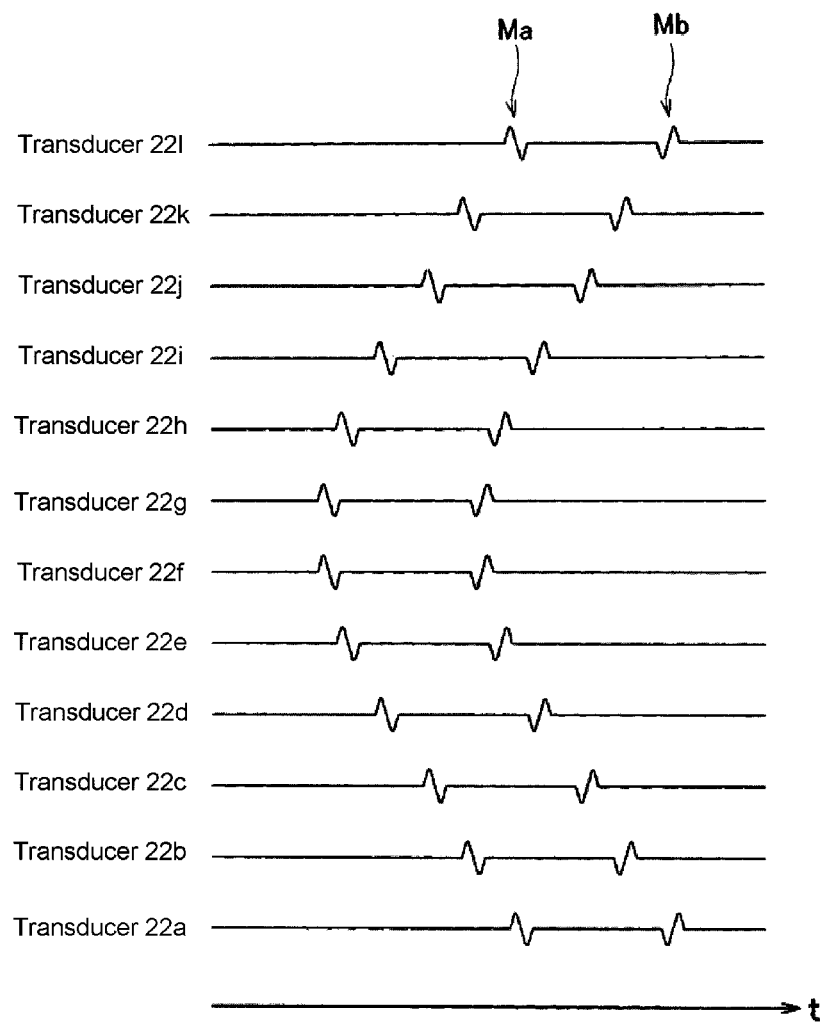
FIG. 3 is a timing chart showing received wave signals of the arrayed transducer.

FIG. 3 shows an example of the received wave signals by the transducers 22a-22l. The horizontal axis of FIG. 3 represents a time after the transmission of the incident wave. A waveform Ma in FIG. 3 represents the front-surface reflected wave, and a waveform Mb represents the back-surface reflected wave. The back-surface reflected wave may be inverted in phase because it goes through acoustic impedance in a reflection from a coarse part (cancellous bone) to a dense part (cortical bone).

Figure 4:
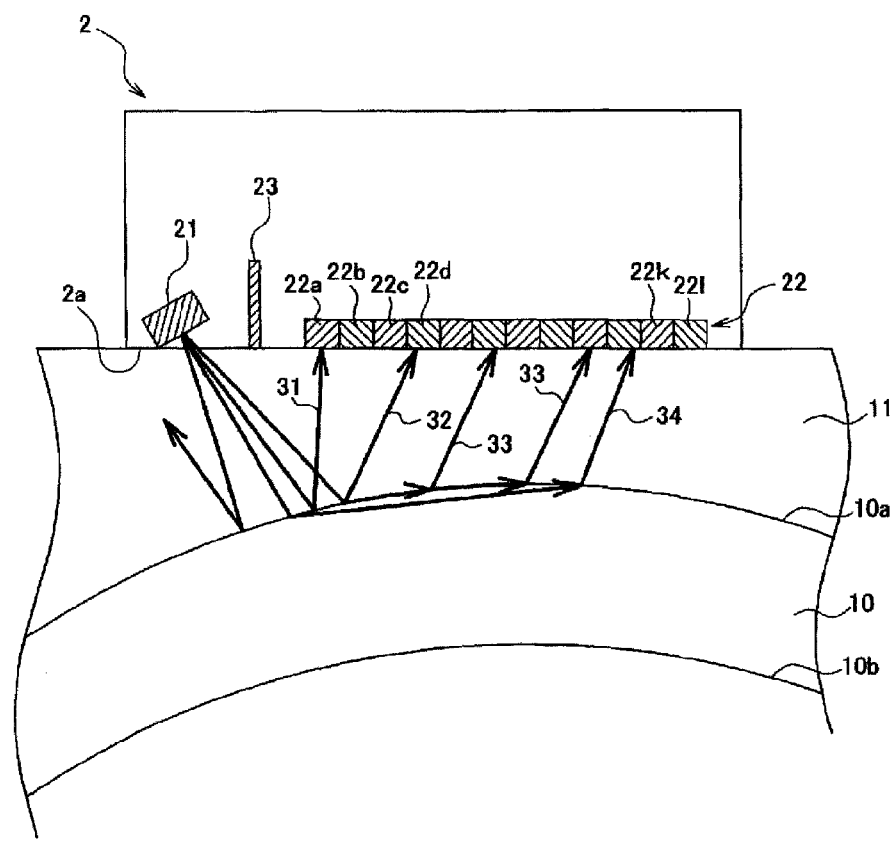
FIG. 4 is a schematic view for illustrating propagation courses of the ultrasonic wave transmitted from a transducer dedicated to wave transmission.

When Ultrasonic Wave is Transmitted from Transducer 21 Dedicated to Wave Transmission When the transmission switching module 5a determines the transducer 21 dedicated to wave transmission to be a transducer that transmits an ultrasonic wave, an electric pulse signal is sent from the transmission circuit 5 to the transducer 21 dedicated to wave transmission, and the transducer 21 dedicated to wave transmission then transmits an ultrasonic wave to the bone 10. As shown in FIG. 4, from the transducer 21 dedicated to wave transmission, an ultrasonic wave with a wide directivity (incident wave) is transmitted. The incident wave that propagates inside of the soft tissues 11 in a direction inclined to the contacting face 2a.

The ultrasonic wave transmitted from the transducer 21 dedicated to wave transmission is received by the arrayed transducer 22 via a plurality of propagation routes. Like the case where an ultrasonic wave is transmitted from the arrayed transducer 22, the transducers 22a-22l transmits the received wave signal to the reception circuits 6a-6l, respectively, when they receive the ultrasonic waves.

There are the following three types exist for the propagation routes of the ultrasonic wave that is transmitted from the transducer 21 dedicated to wave transmission and reaches the arrayed transducer 22. One route is a propagation route where the ultrasonic wave that propagates along the surface of the soft tissues 11 and then reaches the arrayed transducer 22 directly. Another route is a propagation route where the ultrasonic wave reflects on the bone front surface 10a and then reaches the arrayed transducer 22 (propagation route including the reflected wave 31 or the reflected wave 32 in FIG. 4). Still another route is a propagation route where the ultrasonic wave that propagates along the bone front surface 10a and after that, it exits to the side of the soft tissues 11 from the bone 10 and then reaches the arrayed transducer 22. Further, there are two types among these three types of the propagation routes as explained below.

When a part of the incident wave is incident on the bone front surface 10a near at a critical angle, a surface wave will occur on the bone front surface 10a. The surface wave that propagates along the bone front surface 10a, while emitting a leaky surface wave in a predetermined direction toward the soft tissues 11 (direction near at the critical angle with respective to the bone front surface 10a). This leaky surface wave is received by the arrayed transducer 22. An ultrasonic wave 33 in FIG. 4 is shown as an example of the leaky surface wave. The critical angle is determined based on the speed of sound in the soft tissues 11 and the speed of sound in the bone 10. Because the transducer 21 dedicated to wave transmission is used as the transducer with a wide directivity, even if the inclination of the bone front surface 10a varies depending on examinees, it is possible to make the ultrasonic wave be incident on the bone front surface 10a near at the critical angle.

When the part of the incident wave is incident on the bone front surface 10a at an angle smaller than the critical angle, it is refracted by the bone front surface 10a and then propagates in the vicinity of the bone front surface 10a of the bone 10, and after that, it is again refracted by the interface 10a of the bone 10 and the soft tissues 11. This refracted wave (hereinafter, referred to as a "bone front-surface refracted wave") is received by the arrayed transducer 22. An ultrasonic wave 34 in FIG. 4 is shown as an example of the bone front-surface refracted wave. The bone front-surface refracted wave is generated only when the shape of the bone front surface 10a is not flat.

Both the bone front-surface refracted wave and the leaky surface wave may be received by a single transducer that constitutes the arrayed transducer 22. The bone front-surface refracted wave may be received before or after the leaky surface wave is received.

When a bone width (a length of the bone 10 in the horizontal direction of FIG. 1) is small, the leaky surface wave may not reach a position distant from the transducer 21 dedicated to wave transmission. That is, the smaller the bone width becomes, the shorter the range within which the leaky surface wave can be received will be. Although it may depend on the inclination of the bone front surface 10a relative to the contacting face 2a, a distance of a transducer among the transducers capable of receiving the leaky surface wave which is the closest to the transducer 21 dedicated to wave transmission and the transducer 21 dedicated to wave transmission will be longer as the thickness of the soft tissues 11 is thicker. In this embodiment, because the leaky surface wave is received by the plurality of transducers 22a-22l, even if the bone width or the thickness of the soft tissues 11 varies for individual examinees, it is possible to certainly receive the leaky surface wave by at least one of the plurality of transducers among the plurality of transducers 22a-22l.

As described above, the leaky surface wave can only be received at a position with some distance from the transducer 21 dedicated to wave transmission. On the other hand, the reflected wave from the bone surface 10a can be received even at a position close to the transducer 21 dedicated to wave transmission. For example, in the case of FIG. 4, the leaky surface wave will be received by the transducer 22d and the transducers on the right of the transducer 22d, but the reflected wave from the bone surface 10a will be received by the transducer 22a and the transducers on the right of the transducer 22a. Thus, the transducers on the side of the transducer 21 dedicated to wave transmission in the arrayed transducer 22 may receive only the reflected wave, and may not receive the leaky surface wave.

When both the leaky surface wave and the reflected wave from the bone front surface 10a are received by one transducer constituting the arrayed transducer 22, the leaky surface wave is received before the reflected wave. This is because a speed of sound in the bone 10 is faster than a speed of sound in the soft tissues 11.

An ultrasonic wave that propagates along the surface of the soft tissues 11 and reaches the arrayed transducer 22 directly (hereinafter, referred to as a "direct wave") reaches a transducer near the transducer 21 dedicated to wave transmission before the leaky surface wave. However, the ultrasonic wave may reach after the leaky surface wave a transducer apart from the transducer 21 dedicated to wave transmission. Note that, due to the existence of the sound insulating material 23, the amplitude of the direct wave is designed to be very small compared with the amplitude of the leaky surface wave or the reflected wave.

Referring back to FIG. 1B, the calculation module 8 includes a CPU, a RAM, and a ROM (these are not illustrated), and also includes a signal processing module 81, a shape detecting module 82, a speed-of-sound deriving module 83, and a bone strength index deriving module 84.

The signal processing module 81 includes a memory module and a signal processing circuit (these are not illustrated). The signal processing module 81 receives the received wave signals transmitted from the reception circuits 6a-6l and stores in the memory module the received wave signals within a predetermined period of time from the wave transmission of the ultrasonic wave. The signal processing module 81 then detects a peak value of the received wave signals with the signal processing circuit, and transmits it to the shape detecting module 82 and the speed-of-sound deriving module 83.

The shape detecting module 82 detects shapes of the bone front surface 10a and the bone back surface 10b by using the received wave signals of the front-surface reflected wave and the back-surface reflected wave of the arrayed transducer 22 when the ultrasonic wave is transmitted from the arrayed transducer 22. The shape detecting module 82 includes an incoming direction detecting module 82a, a propagation time detecting module 82b, a front-surface reflection point detecting module 82c, a shape deriving module 82d, and a back-surface reflection point detecting module 82e.

The incoming direction detecting module 82a determines eleven transducer groups 22A-22K (refer to FIG. 1), each group having adjacent two transducers among the twelve transducers 22a-22l, and detects incoming directions of the front-surface reflected waves and the back-surface reflected waves that reach each of the transducer groups 22A-22K.

The propagation time detecting module 82b detects a propagation time of the front-surface reflected wave and a propagation time of the back-surface reflected wave that reach each of the transducer groups 22A-22K.

The front-surface reflection point detecting module 82c detects eleven reflection points on the bone front surface 10a (front-surface reflection points) based on the incoming directions and the propagation times of the front-surface reflected waves which reached the eleven transducer groups 22A-22K and which are detected by the incoming direction detecting module 82a and the propagation time detecting module 82b, respectively.

The shape deriving module 82d derives a shape of the bone front surface 10a using the eleven front-surface reflection points detected by the front-surface reflection point detecting module 82c. Further, the shape deriving module 82d derives a shape of the bone back surface 10b using the eleven back-surface reflection points detected by the back-surface reflection point detecting module 82e described later, and also derives a thickness of the bone 10 (cortical bone) based on the shapes of the bone front surface 10a and the bone back surface 10b.

The back-surface reflection point detecting module 82e detects eleven reflection points on the bone back surface 10b (back-surface reflection points) based on the incoming directions and the propagation times of the back-surface reflected waves which reach the eleven transducer groups 22A-22K, respectively and which are detected by the incoming direction detecting module 82a and the propagation time detecting module 82b.

The speed-of-sound deriving module 83 derives a speed of sound of the ultrasonic wave that propagates along the bone front surface 10a based on the received wave signal of the leaky surface wave or the bone front-surface refracted wave of the arrayed transducer 22 and the shape of the bone front surface 10a derived by the shape deriving module 82d when the ultrasonic wave is transmitted from the transducer 21 dedicated to wave transmission.

The bone strength index deriving module 84 derives an index related to a strength of the bone using the speed of sound in the two directions of the bone 10 derived by the speed-of-sound deriving module 83 and the thickness of the bone 10 derived by the shape deriving module 82d.

The display module 9 is connected with the calculation module 8 to display the shapes of the bone front surface 10a and the back surface 10b derived by the shape deriving module 82d, and a diagnostic index of the bone strength derived by the bone strength index deriving module 84.

Figure 5:
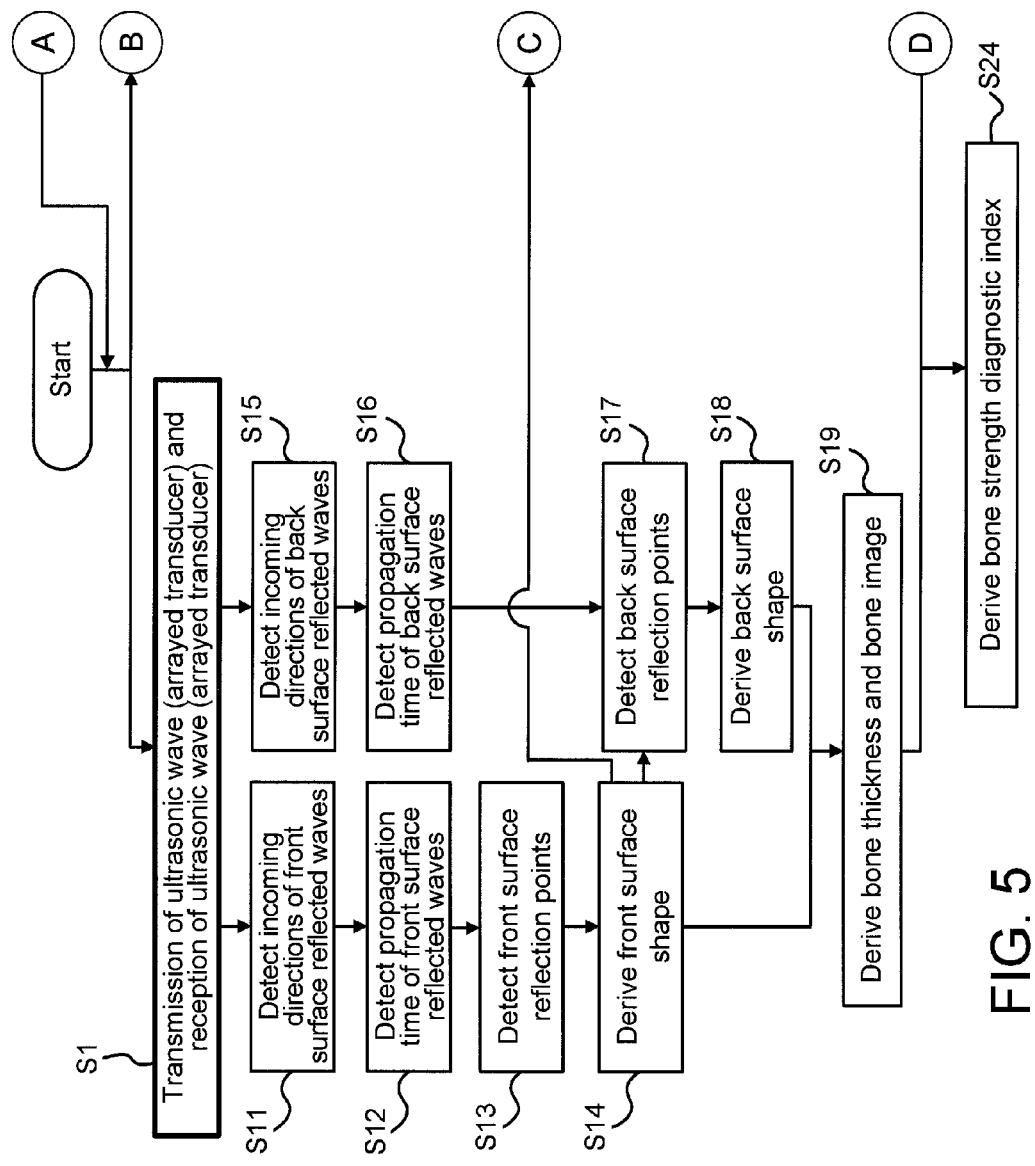
FIGS. 5 and 5B are a flowchart showing an operation of a bone strength diagnostic device.
Figure 5B:
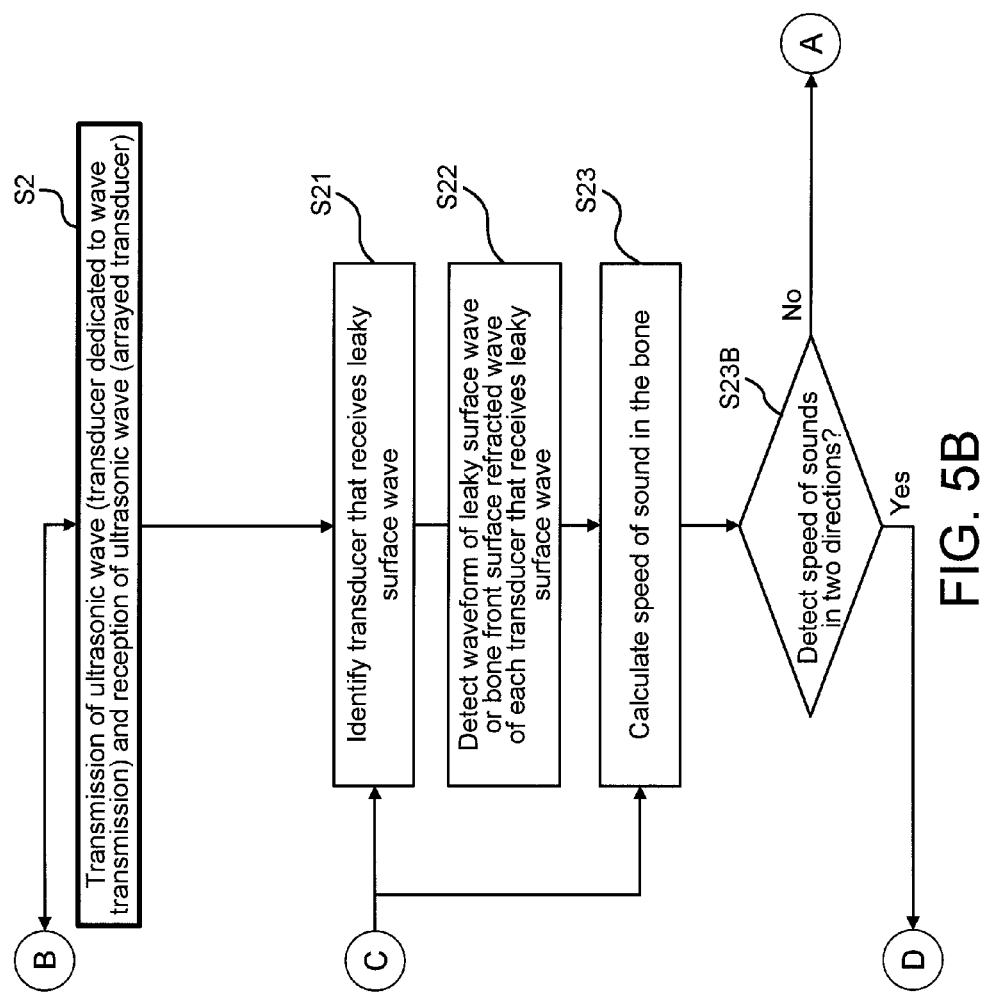

Next, an operation of the bone strength diagnostic device 1 is explained particularly focusing on an operation of the calculation module 8. FIGS. 5 and 5B are a flowchart showing the operation of the bone strength diagnostic device 1.

As shown in FIGS. 5 and 5B, the arrayed transducer 22 performs wave transmission and wave reception of ultrasonic waves (S1), and then, the transducer 21 dedicated to wave transmission transmits an ultrasonic wave without moving the position of the ultrasonic transceiver 2 and the ultrasonic wave is received by the arrayed transducer 22 (S2).

Shape Detection Step

The shape detecting module 82 derives a shape of the bone front surface 10a using the received wave signals of the arrayed transducer 22 when the ultrasonic wave is transmitted from the arrayed transducer 22. First, the incoming direction detecting module 82a detects respective incoming directions of the front-surface reflected waves for the eleven transducer groups 22A-22K (S11).

Two incoming directions of the front-surface reflected waves for two adjacent transducers constituting each transducer group (for example, the transducers 22a and 22b) are close to each other. Therefore, the incoming direction detecting module 82a detects one incoming angle per one transducer group considering that the two incoming directions are the same. Hereinafter, a method of detecting the incoming angle with respect to the transducer group 22A is explained in detail.

Figure 6A:
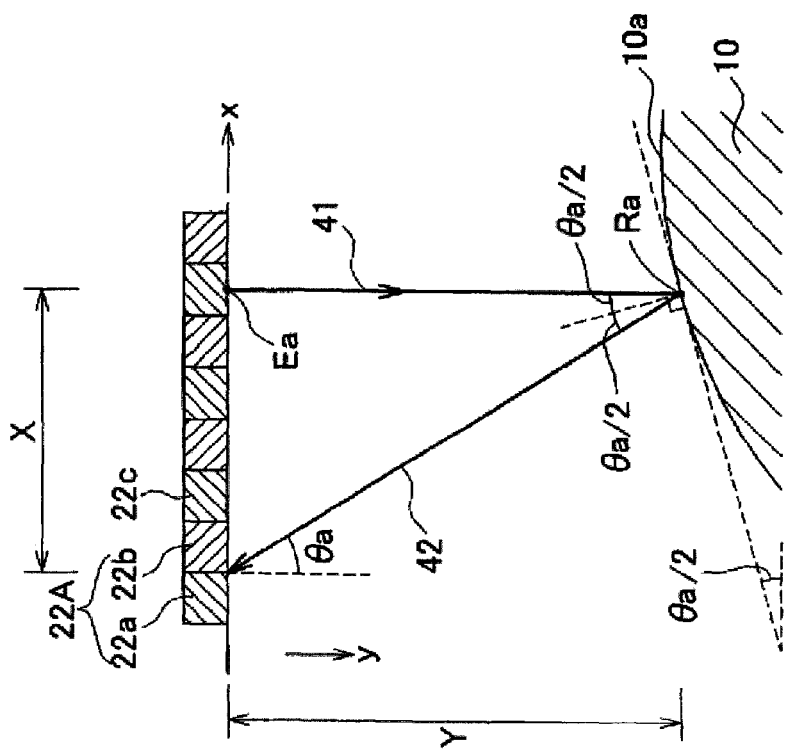
FIG. 6A is a schematic view for illustrating a method of detecting a front-surface reflection point.
Figure 6B:
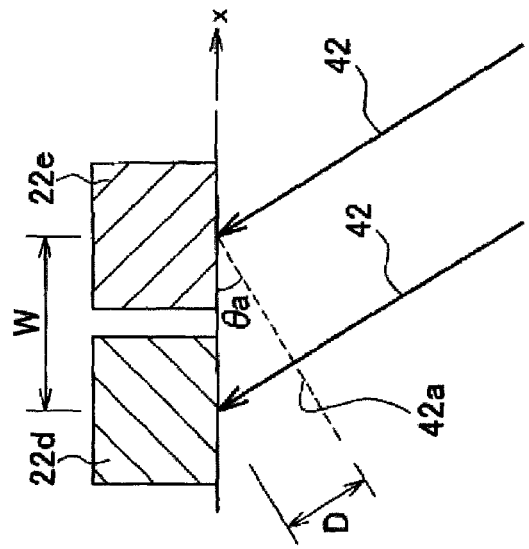
FIG. 6B is a schematic view for illustrating a method of detecting an incoming direction.

As shown in FIG. 6A, it is assumed that the incoming angle of the front-surface reflected wave 42 that reaches the transducer group 22A is set to θa. In this case, as shown in FIG. 6B, because the incoming angles of the front-surface reflected waves that reaches the two transducers 22a and 22b is θa, a wave face 42a of the front-surface reflected waves 42 is inclined at the angle θa with respect to the arranged direction of the arrayed transducer 22 (the x-axis direction in FIG. 6B). Therefore, one front-surface reflected wave 42 reaches the transducer 22b after another front-surface reflected wave 42 reached the transducer 22a, which further travels by a distance D. That is, the transducer 22b receives the front-surface reflected wave 42 after the transducer 22a. Here, the time difference between the times at which the two transducers 22a and 22b receive the front-surface reflected wave 42 are set to Δt.

The following method may be used for deriving Δt based on the received wave signals of the transducers 22a and 22b. For example, a time difference between maximum peaks of the received wave signals of the two transducers 22a and 22b may also be used. Alternatively, so called the "zero-crossing method" may be used in which a time difference between intersecting point of rising parts of the maximum peaks of the received wave signals of the two transducers 22a and 22b with the line of zero amplitude may also be used. Alternatively, a correlation processing with a waveform stored in advance in the calculation module 8 may also be performed to derive the time difference Δt. Alternatively, a phase difference between the received wave signals of the two transducers 22a and 22b may also be obtained by the quadrature detection method or the like to derive the time difference Δt with the obtained phase difference and the frequency of the incident wave. Note that this method can be used only when the phase difference between the received wave signals of the two transducers 22a and 22b is 180 degrees or less.

If a speed of sound in the soft tissues 11 is assumed to be Vs, the difference D of the propagation course can be calculated by $D=Vs*\Delta t$. As shown in FIG. 6B, when an interval between the two transducers 22a and 22b is assumed to be W, the difference D of the propagation course can be expressed by $D=W-\sin \theta a$. Therefore, the incoming angle θa can be calculated by $\theta a=\arcsin(Vs*\Delta t/W)$. Although the measured value may be used for the speed of sound Vs in the soft tissues 11, an assumed value may also be used.

As described above, although the method of detecting the incoming angle θa of the front-surface reflected wave 42 with respect to the transducer group 22A is explained, the incoming angles θa for other ten transducer groups 22B-22K may also be detected with a similar procedure.

When detecting the incoming direction, the incoming angle may be directly detected from the phase difference between the received wave signals of two transducers constituting a transducer group. The term used herein "using a time difference between timings at which the wave-reception transducers receive a front-surface reflected wave, respectively" of the incoming direction detecting module of this embodiment also includes when using a phase difference.

Next, the propagation time detecting module 82b detects propagation times Ta after the ultrasonic wave is transmitted by the arrayed transducer 22 until the front-surface reflected waves reach the transducer groups 22A-22K using the received wave signals of the two transducers 22a and 22b (S12). Although an average value of times after the ultrasonic wave is transmitted by the arrayed transducer 22 until the front-surface reflected waves 42 reach the transducers 22a and 22b may be used for the propagation times Ta, values other than the average value may also be used. When the average value is used, errors in the detected shape of the bone front surface 10a can be reduced.

Next, the front-surface reflection point detecting module 82c detects the front-surface reflection points on the bone front surface 10a using the incoming angles θa and the propagation times Ta of the front-surface reflected waves which reach the transducer groups 22A-22K, respectively (S14). Hereinafter, the method of detecting a position of one front-surface reflection points on the bone front surface 10a is explained using the incoming angles θa with respect to the transducer group 22A.

As shown in FIG. 6A, when the incoming angle of the front-surface reflected wave 42 with respect to the transducer group 22A is θa, this front-surface reflected wave 42 is a reflection of the incidence wave 41, which is transmitted from a point Ea on the surface of the transducers 22a-22l and travels in the y-axis direction in FIG. 6A, on a point (front-surface reflection point) Ra on the bone front surface 10a inclined at θa/2 from the x-axis direction.

Here, as shown in FIG. 6A, a distance from the transducer group 22A in the x-axis direction to the surface reflection point Ra is set to X, and a distance from the transducer group 22A in the y-axis direction to the surface reflection point Ra is set to Y.

Because the propagating direction of the incident wave 41 is the y-axis direction, a distance from the point Ea to the surface reflection point Ra is Y. In addition, because a distance from the surface reflection point Ra to the transducer group 22A can be expressed by $Y/\cos \theta a$, a propagation distance La after the incident wave 41 is transmitted from the point Ea until the front-surface reflected wave 42 reaches the transducer group 22A can be expressed by $La=Y+Y/\cos \theta a$. In addition, the propagation distance La can be calculated by $La=Vs*Ta$ from the propagation time Ta and the speed of sound Vs in the soft tissues. Therefore, Y can be calculated by $Y=Vs*Ta*\cos \theta a/(1+\cos \theta a)$, and X can be calculated by $X=Vs*Ta*\sin \theta a/(1+\cos \theta a)$. Thus, the position of the surface reflection point Ra can be detected.

The propagating direction of the ultrasonic wave (plane wave) transmitted from the arrayed transducer 22 is known beforehand. Therefore, even if it is not determined from which transducer the front-surface reflected wave 42 received in the transducer group 22A is transmitted, the position of the surface reflection point Ra can be detected by using the incoming angle θa and the propagation time Ta which are detected.

As described above, the method of detecting the position of one front-surface reflection point Ra is explained using the incoming angle θa and the propagation time Ta of the front-surface reflected wave that reaches the transducer group 22A. However, the positions of the surface reflection points Ra can be detected with a similar procedure for other ten transducer groups 22B-22K.

In the method described above, the average value of the propagation times of the front-surface reflected waves received by the two transducers constituting a transducer group is set to be the propagation time Ta. However, a propagation time of the front-surface reflected wave received by one of the two transducers may be set to the propagation time Ta as it is. In this case, it may be desirable to use two transducers constituting each transducer group, the received wave signals of the front-surface reflected waves of which are in the same spatial relationship. For example, when using the received wave signal of the transducer 22b in the transducer group 22A, the received wave signal of the transducer 22c is used in the transducer group 22B.

Further, two reflection points may be detected for one transducer group using propagation times and the incoming angle θa of the front-surface reflected waves received by two transducers constituting the transducer group. The term used herein "the propagation time of the front-surface reflected wave that reaches each transducer group" of the propagation time detecting module includes a case where the propagation times of the front-surface reflected waves received by the two transducers are used as "the propagation time of the front-surface reflected wave that reaches each transducer group" as they are.

Figure 7:
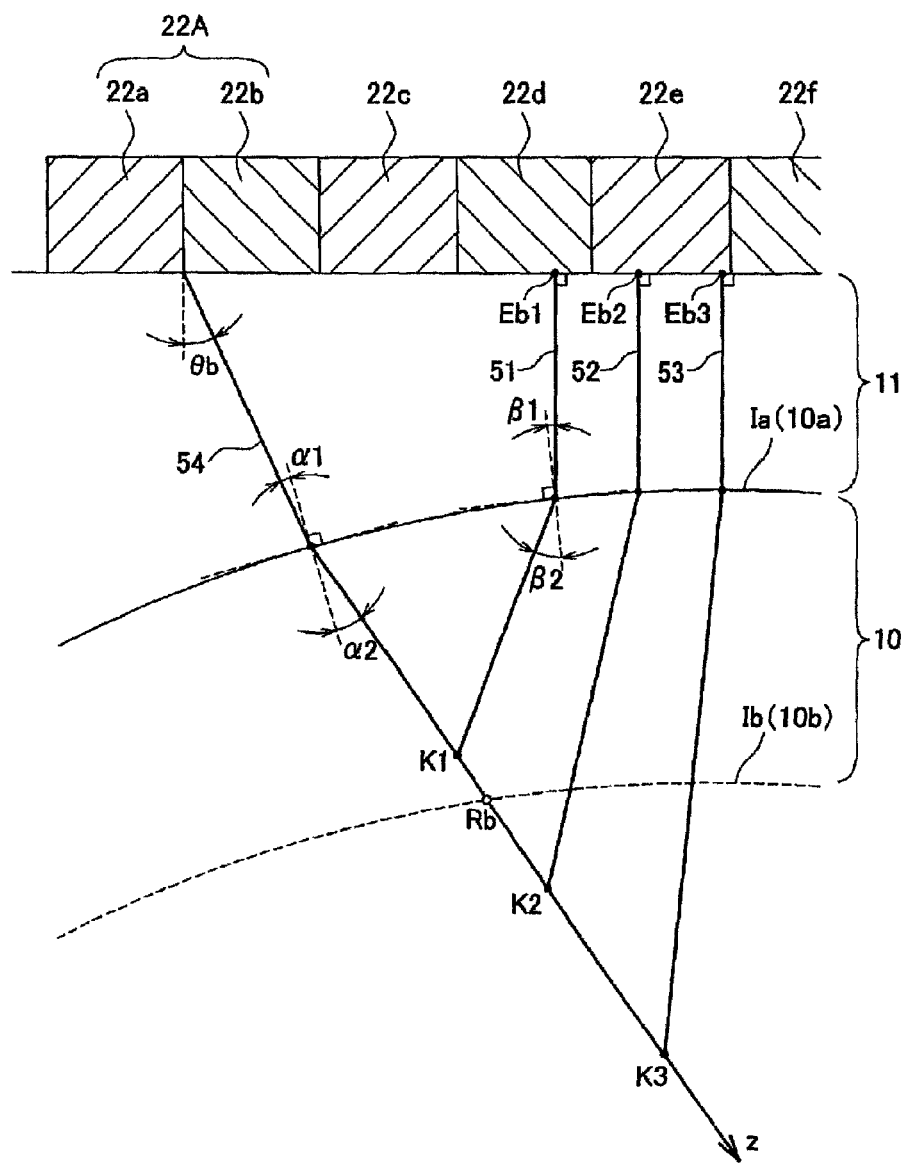
FIG. 7 is a schematic view for illustrating a method of detecting a back-surface reflection point.

The shape deriving module 82d derives a bone front surface line Ia in the x-y plane as shown in FIG. 7 connecting the eleven surface reflection points Ra detected by the front-surface reflection point detecting module 82c with a straight line or a curve (S13). The bone front surface line Ia is displayed on the display module 9 together with a bone back surface line Ib derived later. A size (outer diameter) of the bone 10 can be estimated by using the bone front surface line Ia. Note that the term used herein "deriving the shape of the bone front surface using a plurality of reflection points" by the shape deriving module is not limited to connecting a plurality of reflection points to derive the front surface line, but may include simply acquiring the spatial relationship of the plurality of reflection points.

Next, the shape of the bone back surface 10b is derived. First, the incoming direction detecting module 82a and the propagation time detecting module 82b detect an incoming direction θb and a propagation time Tb0 of a back-surface reflected wave, respectively, that reaches each of the transducer groups 22A-22K by a similar method to the case of the front-surface reflected wave 42 (S15, S16). Note that, because there is a time difference as shown in FIG. 3 between the received wave signal of the front-surface reflected wave and the received wave signal of the back-surface reflected wave for each transducer, they are easily distinguishable.

Next, the back-surface reflection point detecting module 82e detects a position of the back-surface reflection point on the bone back surface 10b using the incoming direction θb and the propagation time Tb0 of the back-surface reflected wave that reaches each of the transducer groups 22A-22K and the bone front surface line Ia derived by the shape deriving module 82d (S17). Hereinafter, a case where one back-surface reflection points on the bone back surface 10b is detected for the transducer group 22A using the incoming angle θb and the propagation time Tb0 is explained.

As shown in FIG. 7, a angle of refraction α1 in the bone front surface 10a of the back-surface reflected wave 54 is calculated from the incoming angle θb of the back-surface reflected wave 54 that reaches the transducer group 22A and the bone front surface line Ia.

If an assumed value of the speed of sound in the bone 10 is Vb', and an angle of incidence of the back-surface reflected wave 54 in the soft tissues 11 is α2, a relation of sin α1-/sin α2=Vs/Vb' can be satisfied by the Snell's law. From this equation, the angle of incidence α2 is calculated, and the propagating direction (z-axis in FIG. 7) in the bone 10 of the back-surface reflected wave 54 is derived.

Further, an angle of incidence β1 of the incident wave 51 to the bone front surface 10a is calculated from the propagating direction (y-axis direction) of the incident wave 51 transmitted from the point Eb1 on the surface of the transducers 22a-22l to the bone front surface 10a, and the bone front surface line Ia.

If an angle of refraction of the incident wave 51 in the bone front surface 10a is set to β2, a relation of sin β1/sin β2=Vs/Vb' can be satisfied by the Snell's law. From this equation, the angle of refraction β2 is calculated, and as shown in FIG. 7, the propagating direction of the incident wave 51 in the bone 10 is derived. An intersecting point of the propagating direction of the incident wave 51 in the bone 10 and the propagating direction (z-axis) of the back-surface reflected wave 54 in the bone 10 is set to K1.

Assuming that the intersecting point K1 is a reflection point on the bone back surface 10b (back-surface reflection point), the incident wave 51 transmitted from the point Eb1 would have reflected on the point K1 in the bone back surface 10b, and will have reached the transducer group 22A. In this assumed propagation route, a predicted value of the propagation time from wave transmission to wave reception is set to Tb1. The Tb1 can be calculated from the propagation route of the ultrasonic wave from the point Eb1 to the transducer group 22A, the speed of sound Vs in the soft tissues 11, and the assumed value Vb' of the speed of sound in the bone 10.

In addition, for the incident waves 52 and 53 transmitted from the points Eb2 and Eb3 on the surface of the transducers 22a-22l, the intersecting points K2 and K3 of the propagating direction in the bone 10 and the z-axis are also detected, respectively, similar to the incident wave 51. Further, the predicted values Tb2 and Tb3 of the propagation time from the wave transmission to the wave reception are calculated when the intersecting points K2 and K3 are set to the back-surface reflection point, respectively.

Figure 8:
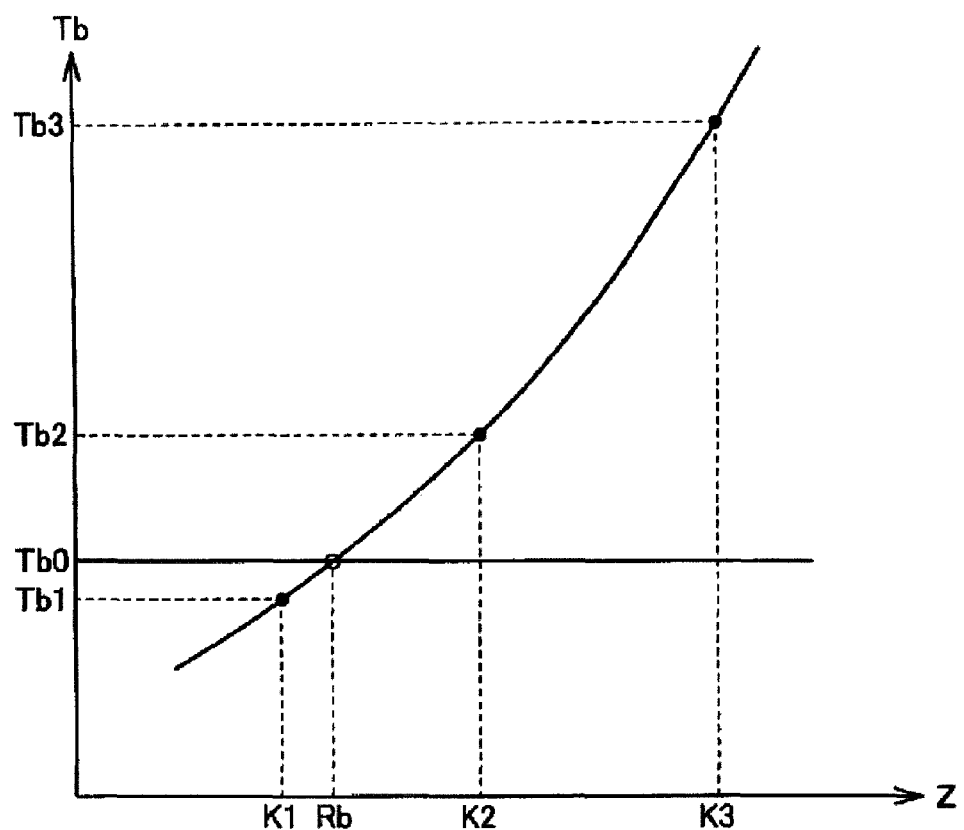
FIG. 8 is a graph to be used for the detection of the back-surface reflection point, showing a relation between a propagation time and a position of the back-surface reflection point.

FIG. 8 shows a graph showing a relation between a position of the back-surface reflection points on the z-axis and the propagation time Tb from wave transmission of the incident wave until the back-surface reflected wave reaches the transducer group 22A. A curve in FIG. 8 connects three points acquired from the predicted values Tb1, Tb2, and Tb3 of the propagation time when assuming the intersecting point K1, K2, and K3 to be the back-surface reflection points. A position of the back-surface reflection points Rb can be detected from an intersecting point of the curve and a line of Tb=Tb0 (actual measurement of the propagation time).

When any of the predicted values Tb1, Tb2, and Tb3 of the calculated propagation time is almost equal to the actual measurement Tb0 of the propagation time, the back-surface reflection points Rb can be detected without using the graph as shown in FIG. 8.

As described above, only the method of detecting one back-surface reflection point Rb using the incoming angle θb and the propagation time Tb0 of the back-surface reflected wave that reaches the transducer group 22A is explained. However, a similar procedure can be applied to the detection at a position of the back-surface reflection points Rb for each of the remaining ten transducer groups 22B-22K.

The shape deriving module 82d derives a bone back surface line Ib in the x-y plane connecting the detected eleven back-surface reflection points Rb with a straight line or a curve, as shown in FIG. 7 with a dashed line (S18).

The derived bone back surface line Ib is displayed on the display module 9 together with the bone front surface line Ia. Thus, an image of the bone can be obtained. Further, the shape deriving module 82d derives a thickness of the bone 10 using the bone front surface line Ia and the bone back surface line Ib (S19).

As explained above, the bone strength diagnostic device 1 of this embodiment simultaneously transmits the ultrasonic waves of the same phase from the plurality of transducers 22a-22l constituting the arrayed transducer 22, and then derives the shape of the bone front surface 10a and the back surface 10b using the reflected waves. Typically, when ultrasonic waves are transmitted from the plurality of transducers at shifted timing or phase from each other (i.e., when sending electric signals to the plurality of transducers at a shifted timing or phase), it may be necessary to have a plurality of transmission circuits or change-over circuits. However, in this embodiment, because the ultrasonic waves of the same phase are simply transmitted simultaneously from the plurality of transducers 22a-22l, it can achieve a configuration in which one transmission circuit 5 is connected to the plurality of transducers 22a-22l. Therefore, the circuit configuration of the transmission end will be comparatively simple, and, as a result, its cost can be reduced.

In addition, because the ultrasonic waves are simultaneously transmitted from the plurality of transducers 22a-22l to detect the bone shape, the time required for the shape detection can be shortened compared with the case where the bone shape is detected by transmitting the ultrasonic waves from the plurality of transducers with the shifted wave transmission timing. Therefore, shifting in the position of the ultrasonic transceiver 2 can be reduced during the transceiving of the ultrasonic waves and, thereby the bone shape can be detected with sufficient accuracy.

In addition, because the plurality of transducers 22a-22l are configured so as to perform the both transmission and reception of the ultrasonic wave, the number of transducers used for the transmission and reception of the ultrasonic wave for detecting the shape of the bone 10 can be reduced, and the cost can be reduced as well.

Speed of Sound Deriving Step

Next, the speed-of-sound deriving module 83 derives a speed of sound in the bone 10 using the received wave signals of the arrayed transducer 22 when transmitting the ultrasonic wave from a transducer 21 dedicated to wave transmission, and the shape of the bone front surface 10a derived by the shape deriving module 82d. First, based on the shape of the bone front surface 10a, a transducer which receives a leaky surface wave is identified from the plurality of transducers 22a-22l (S21). Hereinafter, it will be explained particularly.

Figure 9:
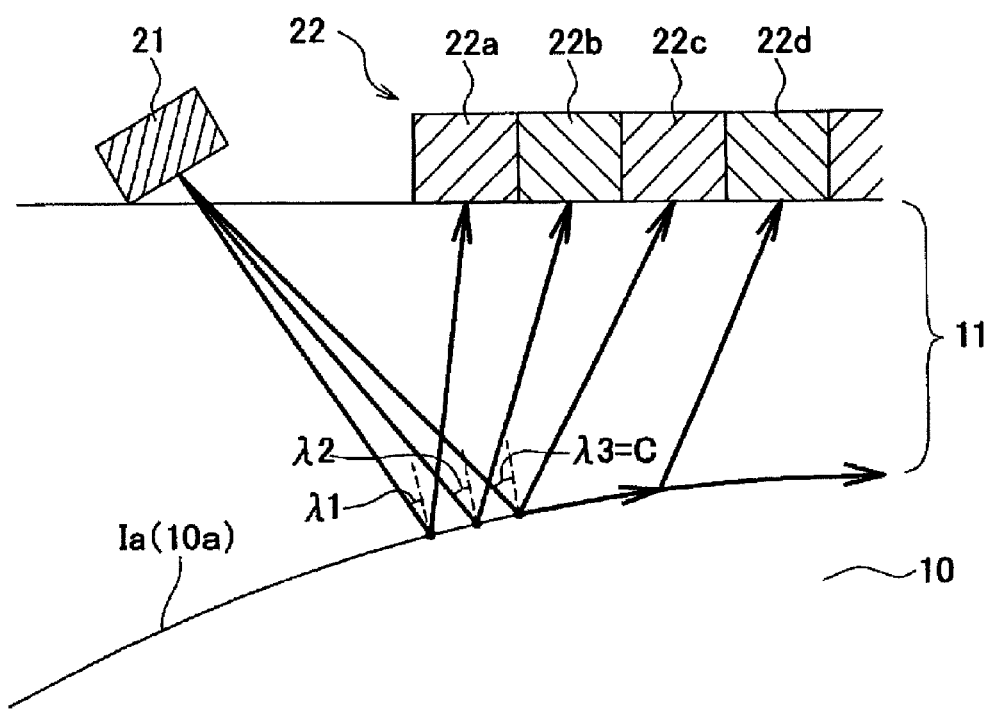
FIG. 9 is a schematic view for illustrating a method to identify a transducer which receives a leaky surface wave.

As shown in FIG. 9, based on the spatial relationship of the transducer 22a, the transducer 21 dedicated to wave transmission, and the bone front surface line Ia, a propagation course of the reflected wave from the bone front surface 10a that reaches the transducer 22a is detected using the Fermat's principle. The Fermat's principle is that an acoustic wave which passes through two points propagates through the shortest course among the propagatable courses. According to the Fermat's principle, the propagation course of the reflected wave that reaches the transducer 22a will be the shortest course where a propagation distance from the transducer 21 dedicated to wave transmission to the transducer 22a among the propagation courses of the reflected wave which can be estimated within a range of directivity of the transducer 21 dedicated to wave transmission.

Next, an angle of incidence $\lambda 1$ on the bone front surface 10a in the propagation course of the reflected wave that reaches the transducer 22a is calculated. Then, from the assumed value Vb' of the speed of sound in the bone 10 and the speed of sound Vs in the soft tissues 11, an assumed value C of a critical angle is calculated, and the assumed value C of the critical angle and the angle of incidence $\lambda 1$ are compared. When the angle of incidence $\lambda 1$ is smaller than the assumed value C of the critical angle, a similar calculation is performed for each transducer the transducer 22b and the transducers on the right of the transducer 22b in the order from the closest to the transducer 21 dedicated to wave transmission until the angle of incidence will be equal to (or greater than) the assumed value C of the critical angle. Here, the angle of incidence $\lambda 3$ in the propagation course of the reflected wave that reaches the transducer 22c is assumed to be equal to the assumed value C of the critical angle. When the angle of incidence is equal to the critical angle, a surface wave occurs on the bone front surface 10a. Therefore, the transducer 22d is identified as the transducer closest to the transducer 21 dedicated to wave transmission that receives a leaky surface wave. That is, the transducer 22d and the transducers on the right of the transducer 22d are identified as the transducers which receive the leaky surface wave.

Note that, as described above, when the bone width (a diameter of the bone 10 in the horizontal direction of FIG. 1) is small, a transducer at a position apart from the transducer 21 dedicated to wave transmission (for example, the transducers 22k and 22l), the leaky surface wave may not reach. In this case, the transducer closest to the transducer 21 dedicated to wave transmission that receives the leaky surface wave may be identified by the above-described method, and to which transducer the leaky surface wave reaches may be identified using the bone front surface line Ia (that is, a transducer capable of receiving the leaky surface waver, which is most separated from the transducer 21 dedicated to wave transmission, may be identified).

Next, a waveform of the leaky surface wave (or the bone front-surface refracted wave) is detected from the received wave signals within a predetermined period of time from the wave transmission, of the transducers 22d-22l identified as the transducers which receive the leaky surface wave (S22). Hereinafter, this will be explained in detail.

Figure 10:
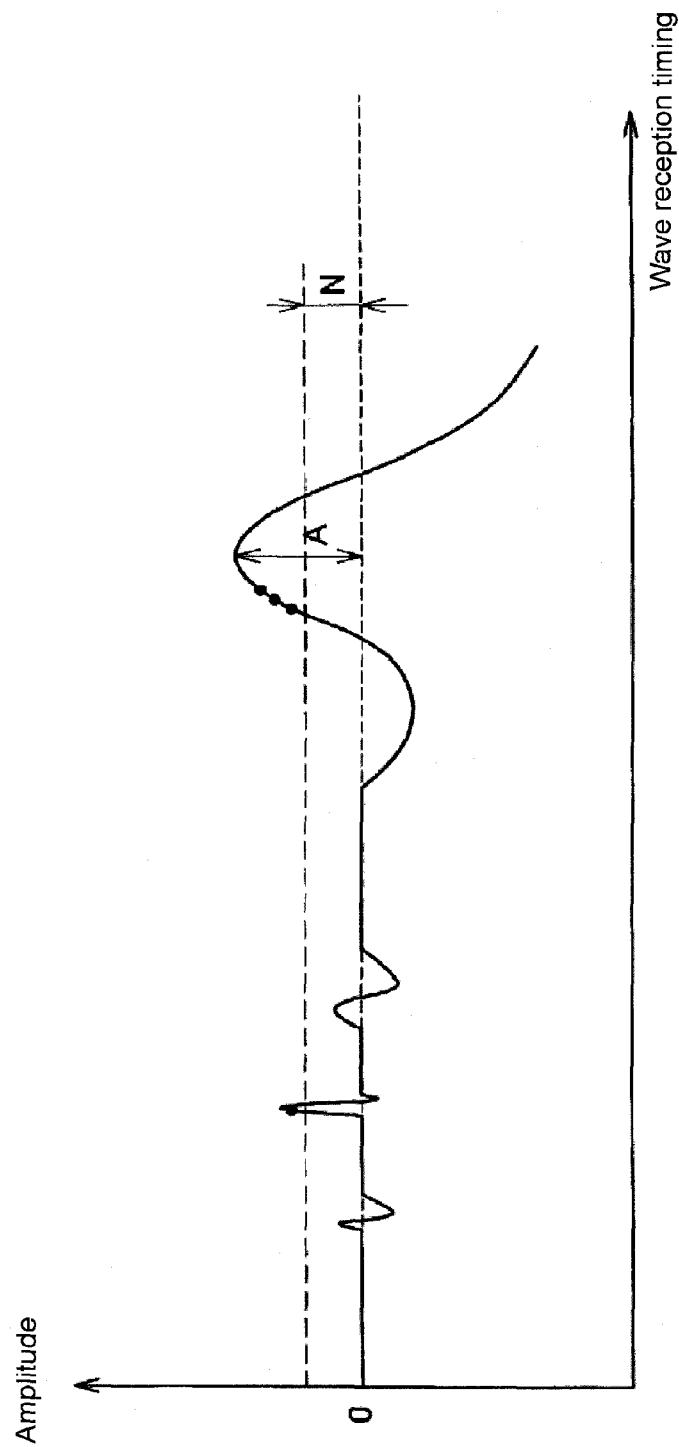
FIG. 10 is a graph for illustrating a method to distinguish a waveform of noise from a waveform of the ultrasonic wave.

Among the received wave signals of the transducers 22d-22l, a waveform of the ultrasonic wave and a waveform of noise are distinguished to detect a waveform of the ultrasonic wave at the earliest wave-reception timing. Specifically, as shown in FIG. 10, a noise threshold N which is slightly greater than a general noise level is set, and when amplitude exceeds the threshold N consecutively at n points (for example, three points), it is determined to be a waveform of the ultrasonic wave, for example.

As described above, when both the leaky surface wave and the reflected wave from the bone front surface 10a reach one transducer, the leaky surface wave reaches before the reflected wave. Thus, by detecting the waveform of the ultrasonic wave at the earliest wave-reception timing, the waveform of the leaky surface wave or the bone front-surface refracted wave can be detected. The propagation time of the leaky surface wave or the bone front-surface refracted wave which reached each of the transducers 22d-22l can be derived from the waveform maximum peak value, the zero-crossing value, etc. Note that, although the direct wave may reach before the reflected wave and the leaky surface wave, because the direct wave is designed so that amplitude of which may be very small compared with the reflected wave and the leaky surface wave as described above, the direct wave may be hardly detectable.

Next, the circumferential speed of sound of the bone front surface 10a is calculated using the received wave signal of the ultrasonic wave at the earliest wave-reception timing (the received wave signal of the leaky surface wave or the bone front-surface refracted wave) of the transducers 22d-22l which are identified as transducers which receive the leaky surface wave, and the shape of the bone front surface 10a (S23).

Figure 11:
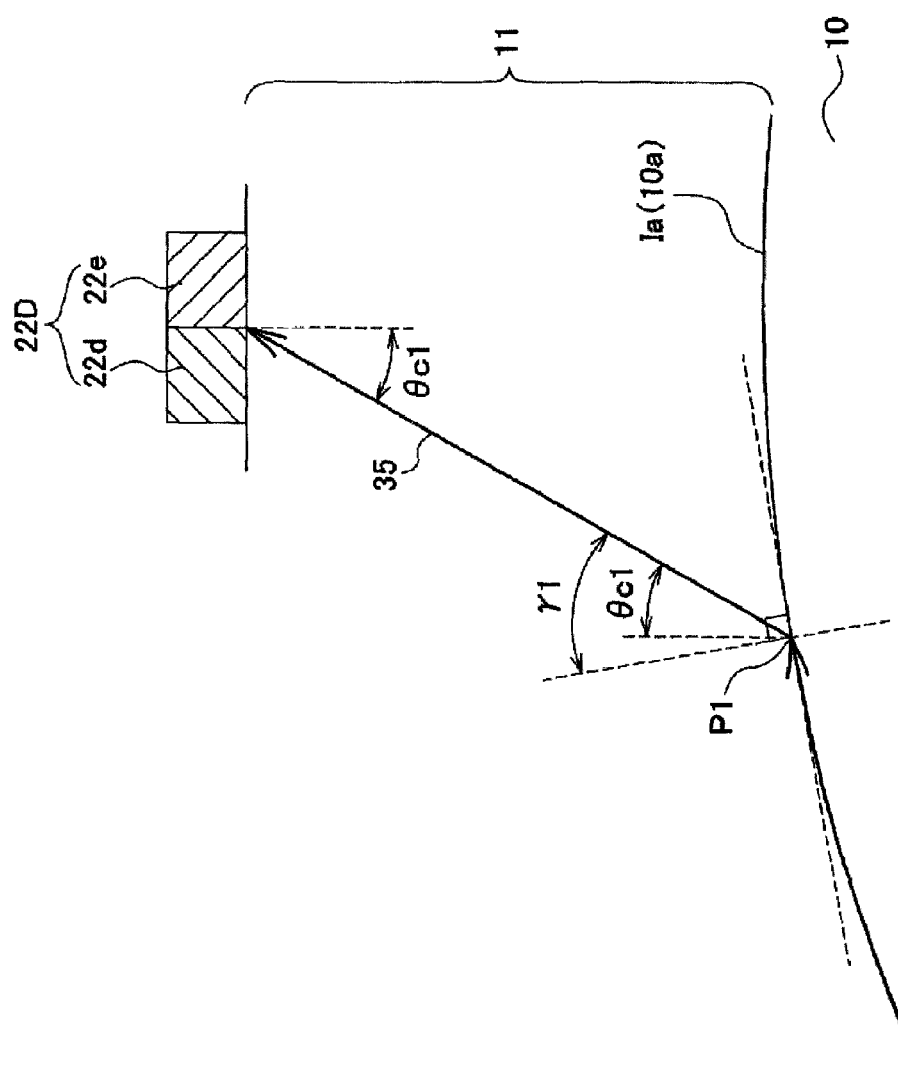
FIG. 11 is a schematic view for illustrating a deriving method of a speed of sound.

First, one transducer group is selected from the plurality of transducers 22d-22l identified as transducers which receive the leaky surface wave. Hereinafter, as shown in FIG. 11, a case where the transducer group 22D having the transducers 22d and 22e is selected will be explained as an example.

First, the waveform of the ultrasonic wave at the earliest wave-reception timing detected from the received wave signals of the transducers 22d and 22e (a waveform of the leaky surface wave or the bone front-surface refracted wave) is assumed to be the waveform of the leaky surface wave. The angle of refraction of the bone surface refracted wave from the bone front surface 10a is very close to the angle of refraction of the leaky surface wave from the bone front surface 10a (the same angle as the critical angle). Therefore, even if the waveform of the ultrasonic wave at the earliest wave-reception timing is a waveform of the bone front-surface refracted wave, the speed of sound can be derived with sufficient accuracy.

It is assumed that the incoming directions of the leaky surface waves that reach the two transducers 22d and 22e approximate with each other, and an incoming angle $\theta c1$ of the leaky surface wave 35 with respect to the transducer group 22D is detected from the time difference between the received wave signals of the leaky surface waves of the two transducers 22d and 22e. As a particular method of detecting the incoming angle $\theta c1$, a similar method to the method of detecting the incoming angles $\theta a$ and $\theta b$ by the incoming angle detecting module may be used (refer to FIG. 6B).

An originating point P1 of the leaky surface wave 35 on the bone front surface 10a is detected from the incoming angle $\theta c1$ and the bone front surface line Ia. An outgoing angle $\gamma 1$ of the leaky surface wave 35 from the bone front surface 10a is calculated from the normal direction at the point P1 on the bone front surface line Ia and the incoming angle $\theta c1$. If a speed of sound in the bone 10 is set to Vb, a relation of $Vb=Vs/\sin \gamma 1$ can be satisfied by the Snell's law. From this equation, the speed of sound Vb of the ultrasonic wave (particularly, the surface wave) that propagates along the bone front surface 10a in the circumferential direction can be calculated.

For all or some selected transducer groups among the plurality of the transducer groups 22E-22K, the speed of sounds Vb in the bone 10 are calculated similarly, and an average value of the plurality of speed of sounds Vb is then calculated. Thus, the speed of sound in the bone 10 can be derived with sufficient accuracy. The speed of sounds Vb derived for the transducer groups 22E-22K can also be mapped on the bone front surface line Ia.

As described above, the speed of sound in the bone 10 is calculated using the information on the shape of the bone front surface 10a. Therefore, even if the shape of the bone front surface 10a is curved, or even if the bone shape inclines to the contacting face 2a, the speed of sound in the bone 10 can be derived with sufficient accuracy. As a result, a diagnostic accuracy of bone strength can be improved.

As described above, although the circumferential speed of sound is derived, alternatively, the ultrasonic transceiver 2 may be installed so that the arrayed direction of the arrayed transducer 22 is substantially in agreement with the longitudinal direction of the bone 10 to derive the longitudinal speed of sound. Note that, because the same bone thickness derived when the cross-sectional shape perpendicular to the longitudinal direction of the bone 10 is derived is used for the thickness of the bone 10, the shape of the bone back surface 10b does not need to be additionally derived in this case.

Finally, the bone strength index deriving module 84 derives an index related to the bone strength using the circumferential speed of sound and the longitudinal speed of sound which are derived by the speed-of-sound deriving module 83, and the shapes of the bone front surface 10a and the bone back surface 10b detected by the shape detecting module 82 (the shape deriving module 82d) (S24). The derived index is displayed on the display module 9.

As described above, the bone strength diagnostic device 1 can obtain the thickness of the bone 10, the image of the bone 10, the circumferential speed of sound, and the longitudinal speed of sound, as the indexes of bone strength or elements for deriving the indexes of bone strength.

The bone has an anisotropy structure and has a structure strong against the direction on which a load acts. In a macroscale, the bone has a long tubular-shaped femur, tibia, or radius, and it has a structure strong against the load direction. In a microscale, the bone has pores of substantially a circular cylinder shape of tens to hundreds of microns. The pores extend substantially in the load direction and, thus, the bone has a structure strong against the load direction. In a nanoscale, the bone has a structure in which biological apatite crystals surrounds collagen fibers. The c-axis of collagen fibers or biological apatite crystals is often oriented in the load direction. Thus, it is important to examine the bone anisotropy structure when diagnosing bone strength.

Recently, it has been said that the bone strength can be expressed with two factors, a bone mass and a bone quality. In addition to a bone size (outer diameter) and a bone thickness which represent the bone mass, examining the anisotropy structure leads to diagnosis of the bone quality.

First, for the bone strength, the bone size (outer diameter) and the cortical bone thickness that constitute the macro structure of a cortical bone are important factors. As described above, the shape deriving module 82d derives the thickness of the cortical bone 10 based on the detected shapes of the bone front surface 10a and the bone back surface 10b, and estimates the size (outer diameter) of the bone 10. Therefore, the index related to the bone mass can be derived by using the thickness of the cortical bone 10 and the size of the bone 10.

The speed of sound of the ultrasonic wave that propagates along the bone surface in the circumferential direction is greatly affected by a percentage of pores, a pore size, and a pore connectivity that constitute the micro structure of the cortical bone. These are factors related to the bone density of the cortical bone. Therefore, the index related to the bone density can be derived by using the circumferential speed of sound.

On the other hand, the speed of sound of the ultrasonic wave that propagates along the bone surface in the longitudinal direction is influenced by both the orientation of the biological apatite crystals that constitute the nanostructure of the cortical bone, and the bone density or pores that constitute the bone micro structure. Therefore, the bone anisotropy structure cannot be estimated only with the longitudinal speed of sound, and it is insufficient for the diagnostic index of bone strength. The index related to the bone orientation can be derived by using both the longitudinal speed of sound and the circumferential speed of sound.

The speed of sound V of the ultrasonic wave which passes through inside of an object can be expressed by the following Equation (1), indicating an elastic characteristic of the bone.

$$V=\sqrt{c/p} \tag{1}$$

Here, c is elastic stiffness and p is density.

Therefore, the circumferential speed of sound and the longitudinal speed of sound may also be used as the indexes of the bone strength as they are. Because the speed of sound V represents an average elastic characteristic including both of the micro structure and the nanostructure, it is characterized in that it can directly show the index of the bone quality related to the bone strength, as compared with X-rays.

As described above, because the bone strength diagnostic device 1 can derive the plurality of indexes related to the bone strength, it is possible to diagnose bone strength in more detail by using these indexes. Note that only one or some of the indexes may be used in this embodiment without using all of the indexes as the index of bone strength.

MODIFIED EMBODIMENTS

Next, modified embodiments to which various changes is made to the previous embodiment will be explained. However, components having a similar configuration to those of the previous embodiment are given with the same reference numerals, and their explanation will be suitably omitted.

Modified Embodiment 1

In the previous embodiment, both the circumferential speed of sound and the longitudinal speed of sound are derived. However, the bone strength may be diagnosed by deriving only the circumferential speed of sound (the thickness of the cortical bone 10).

Modified Embodiment 2

The calculation module 8 may include a damping coefficient detecting module that detects a damping coefficient of the ultrasonic wave received by each transducer based on the transmitted wave signal of the transducer 21 dedicated to wave transmission and the received wave signal of each of the transducers 22a-22l. A particular operation in this modified embodiment is explained below.

First, the damping characteristic detecting module calculates a spectrum of the leaky surface wave (or the bone front-surface refracted wave) received by each of the transducers 22a-22l and a spectrum of the ultrasonic wave transmitted from the transducer 21 dedicated to wave transmission with the Fourier transform to detect a spectrum ratio of the received wave signal of each of the transducers 22a-22l with respect to the transmitted wave signal.

Generally, because an attenuation rate of the ultrasonic wave that propagates inside of a living body is greater in a high-frequency component of the ultrasonic wave than a low-frequency component, the detected spectrum ratio has a certain inclination. By calculating this inclination, a damping coefficient (BUA: Broadband Ultrasonic Attenuation [dB/MHz]) can be detected.

The detected damping coefficients (BUA) of the plurality of transducers 22a-22l are displayed on the display module 9. By using the damping coefficients (BUA) of the plurality of transducers 22a-22l, the bone strength can be diagnosed in more detail.

Modified Embodiment 3

The maximum amplitudes of the leaky surface waves (or the bone front-surface refracted waves) received by the transducers 22a-22l may be displayed on the display module 9, for example, and the bone strength may be diagnosed using these amplitudes.

Modified Embodiment 4

Figure 12:
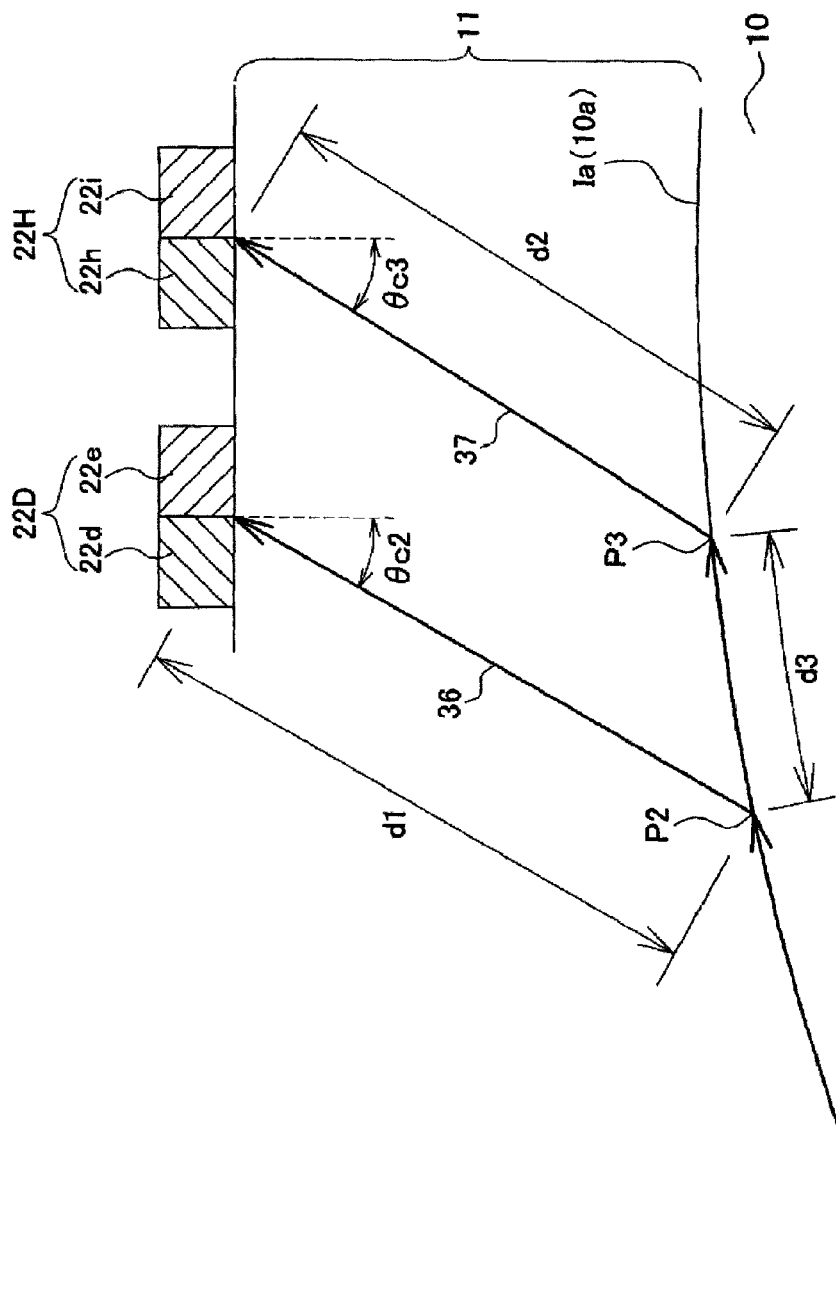
FIG. 12 is a schematic view for illustrating a deriving method of the speed of sound according to Modified Embodiment 4.

As the method of deriving the speed of sound in the bone 10, the following method may also be used. First, two transducer groups (i.e., two groups of transducers, each including a pair of transducers) are selected from the plurality of transducers identified as transducers that receive the leaky surface wave. Preferably, the transducers to be selected do not overlap within the same transducer group or over the transducer groups. Hereinafter, as shown in FIG. 12, a case where the transducer group 22D having the transducers 22d and 22e, and the transducer group 22H having the transducers 22h and 22i are selected will be explained as an example.

Similar to the previous embodiments, assuming that the waveform of the leaky surface wave or the bone front-surface refracted wave detected from the received wave signals of the transducers 22d, 22e, 22h, and 22i is the waveform of the leaky surface wave, The incoming angles θc2 and θc3 of the leaky surface waves 36 and 37 to the two transducer groups 22D and 22H are detected, respectively.

The originating points P2 and P3 of the leaky surface waves 36 in the bone front surface 10a are detected from the incoming angles θc2 and θc3, and the bone front surface line Ia, respectively. Then, a distance d1 from the transducer group 22D to the point P1, a distance d2 from the transducer group 22H to the point P2, and a distance d3 between the points P1 and P2 are calculated.

When the time difference between the times at which the two transducer groups 22D and 22H received the leaky surface waves 36 is set to ΔTc, the time difference ΔTc can be expressed by ΔTc=(d3/Vb)−{(d1−d2)/Vs} from the difference in the propagation routes of the ultrasonic wave that reaches the two transducer groups 22D and 22H. The ΔTc can be calculated using the wave-reception timings of the leaky surface wave of the four transducers 22d, 22e, 22h, and 22i. Therefore, the speed of sound Vb in the bone 10 can be calculated from the equation of Vb=d3/{ΔTc+(d1−d2)/Vs}.

Modified Embodiment 5

As the method of deriving the speed of sound in the bone 10, the following methods may also be used. First, one transducer group is selected from the plurality of transducers identified as transducers that receive the leaky surface wave. Hereinafter, as shown in FIG. 13, a case where the transducer group 22D having the transducers 22d and 22e is selected is explained as an example.

Assuming that the waveform of the leaky surface wave or the bone front-surface refracted wave detected based on the received wave signals of the transducers 22d and 22e is the waveform of the bone front-surface refracted wave, an incoming angle θc4 of the bone front-surface refracted wave 38 with respect to the transducer group 22D is calculated. Then, from the incoming angle θc4 and the bone front surface line Ia, an outgoing point (refracted point) P4 of the bone front-surface refracted wave 38 in the bone front surface 10a is detected. Then, an outgoing angle (angle of refraction) γ4 of the bone front-surface refracted wave 38 is calculated from the normal direction at the point P4 on the bone front surface line Ia and the incoming angle θc4.

The bone front-surface refracted wave 38 that propagates inside of the bone is generated by an ultrasonic wave 39 refracted on the bone front surface 10a. When an angle of incidence of the ultrasonic wave 39 to the bone front surface 10*a* is φ, the speed of sound Vb in the bone 10 (i.e., the speed of sound of the ultrasonic wave 39) can be expressed by Vb=Vs−sin φ/sin γ4 by the Snell's law.

Figure 13:
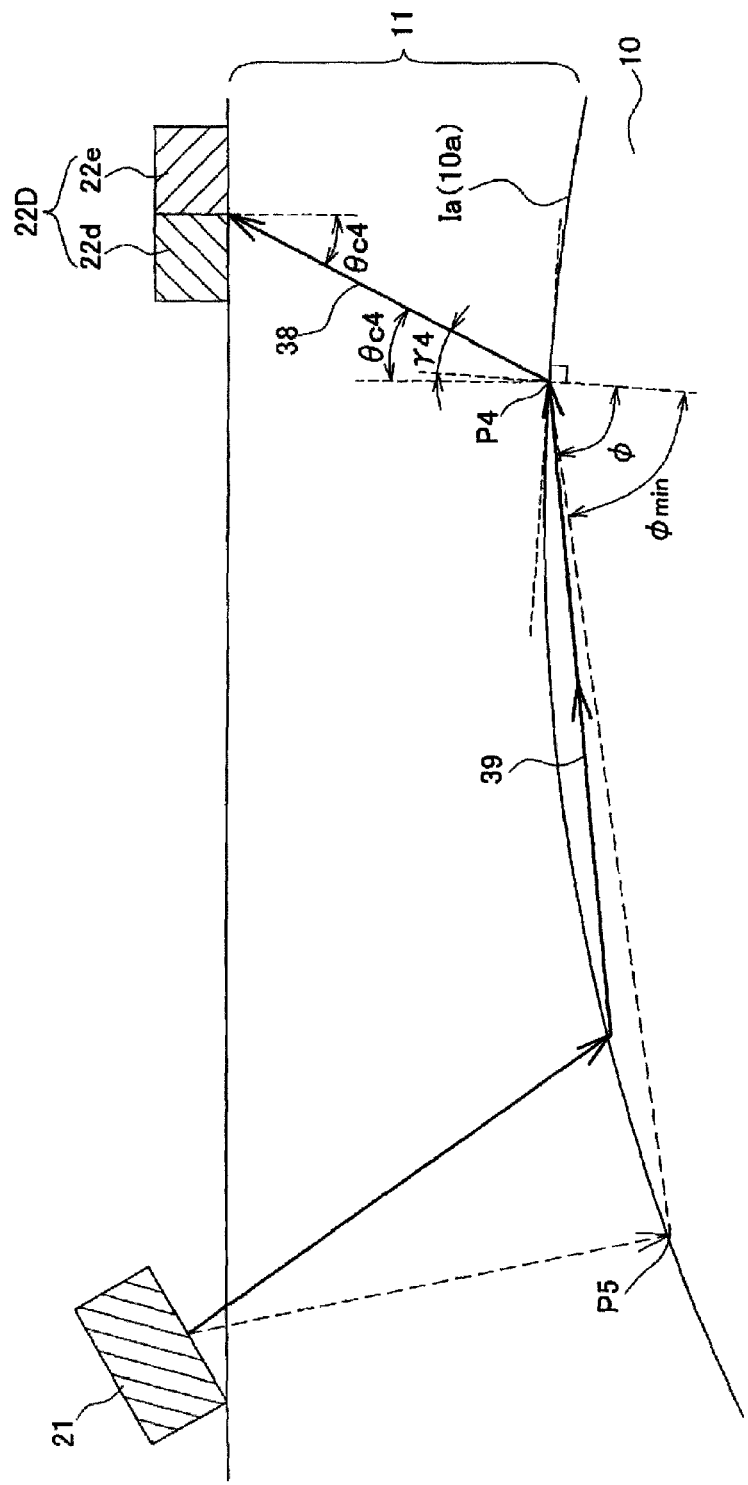
FIG. 13 is a schematic view for illustrating a deriving method of the speed of sound according to Modified Embodiment 5.

Next, based on the angle range of the ultrasonic wave transmitted from the transducer 21 dedicated to wave transmission, a position P5 of the left end part in FIG. 13 is detected within the incident range of the ultrasonic wave on the bone front surface 10*a*. An angle of incidence φmin is calculated assuming that the ultrasonic wave 39 propagates from the point P5 to the point P4. The point P5 will be a position beyond a range of the bone shape derived by the shape deriving module 82*d*. Therefore, the point P5 is detected using the bone shape predicted from the bone shape within the range derived by the shape deriving module 82*d*.

Figure 14:
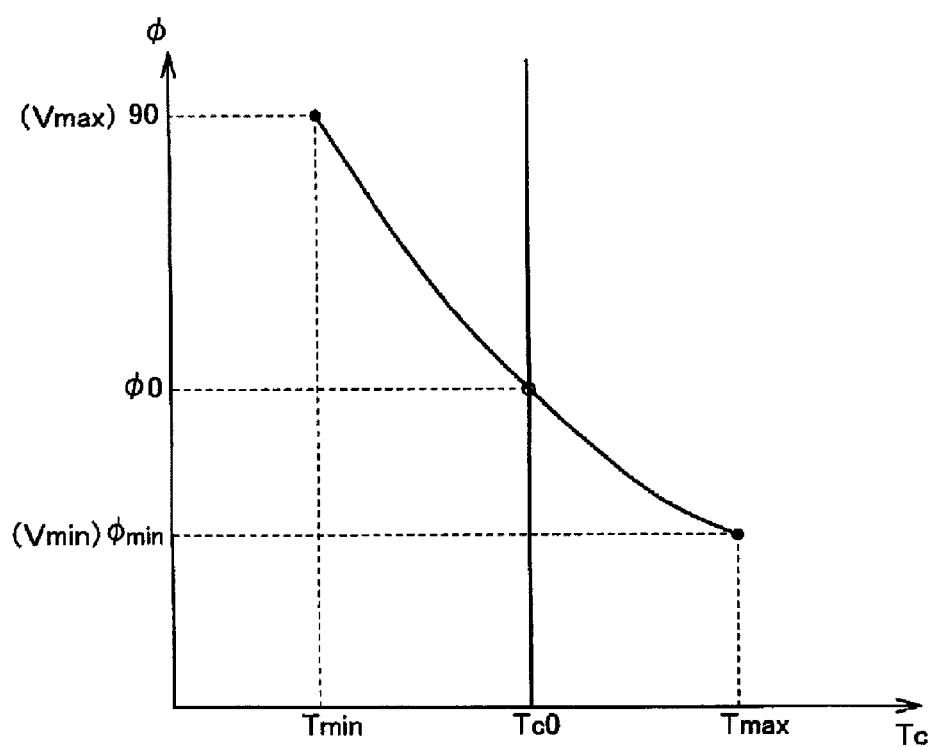
FIG. 14 is a graph to be used for deriving the speed of sound by Modified Embodiment 5, showing a relation between an angle of incidence and a propagation time.

The angle of incidence φ is an angle within a range from φmin to 90 degrees. The speed of sound Vb is a speed within a range of Vmin (Vmin=Vs−sin φmin/sin γ4) to Vmax (Vmax=Vs/sin γ4). FIG. 14 is a graph showing a relation between the angle of incidence φ and a propagation time Tc from wave transmission to wave reception. The curve in FIG. 14 shows the propagation time Tc in the propagation course of each angle of incidence φ when changing the angle of incidence φ from φmin to 90 degrees. The propagation time Tc at a certain angle of incidence φ is calculated from the propagation course length according to the angle of incidence φ, the speed of sound Vb in the bone according to the angle of incidence φ, and the speed of sound Vs in the soft tissues.

An actual measurement Tc0 of the propagation time is calculated from the received wave signals of the transducers 22*d* and 22*e*. An angle of incidence φ0 is derived from an intersecting point of the curve of FIG. 14 and the line of Tc=Tc0. The speed of sound Vb in the bone 10 is calculated using the angle of incidence φ0. Thus, the speed of sound Vb of the ultrasonic wave that propagates inside of the bone 10 in the circumferential direction (particularly, the ultrasonic wave that propagates in the vicinity of the bone front surface 10*a* of the bone 10) can be derived.

Modified Embodiment 6

In the previous embodiments, an ultrasonic wave is transmitted from the arrayed transducer 22, and after a predetermined period of time after that, another ultrasonic wave is transmitted from the transducer 21 dedicated to wave transmission. However, the ultrasonic waves may be simultaneously transmitted from the arrayed transducer 22 and the transducer 21 dedicated to wave transmission.

In this case, different transmission circuits may be connected to the arrayed transducer 22 and the transducer 21 dedicated to wave transmission, and the ultrasonic waves of different frequencies may be transmitted from the arrayed transducer 22 and the transducer 21 dedicated to wave transmission.

Modified Embodiment 7

Figure 15A:
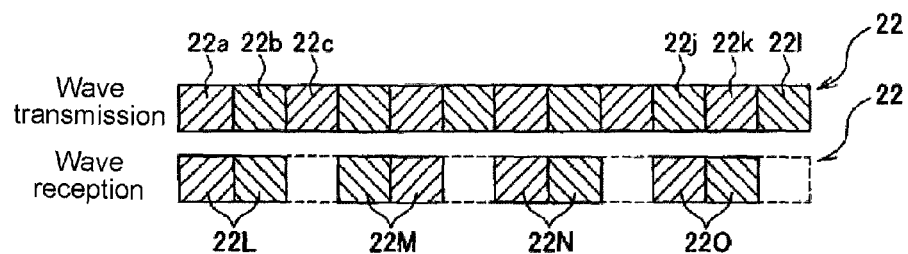
FIGS. 15A to 15C are schematic views of arrayed transducers, where

Although the plurality of transducers that constitute the arrayed transducer 22 perform both wave transmission and wave reception in the previous embodiments, only some transducers among the twelve transducers 22*a*-22*l* may be configured so as to perform the reception of the ultrasonic wave. Particularly, for example, as shown in FIG. 15A, eight transducers 22*a*, 22*b*, 22*d*, 22*e*, 22*g*, 22*h*, 22*j*, and 22*k* among the twelve transducers 22*a*-22*l* may be connected with eight reception circuits to respectively perform the wave reception of the ultrasonic waves. In this case, the incoming direction detecting module 82*a* may determine four transducer groups 22L-22O where each transducer group is constituted with two adjacent transducers.

Modified Embodiment 8

Figure 15B:
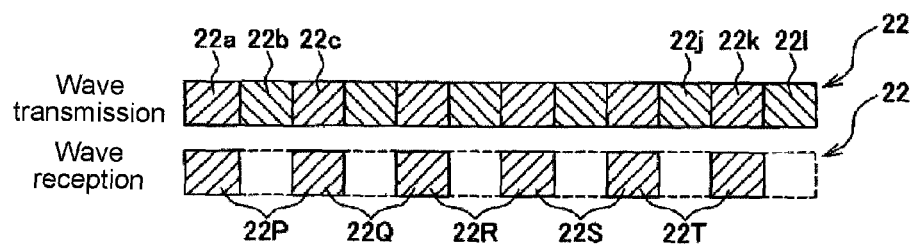

Moreover, for example, as shown in FIG. 15B, alternately selected six transducers from the twelve transducers 22*a*-22*l* (for example, the transducers 22*a*, 22*c*, 22*e*, . . . , and 22*k*) may only perform wave reception of the ultrasonic wave. In this case, the incoming direction detecting module 82*a* may determine five sets of transducers 22P-22T where alternately selected two transducers constitute a transducer group.

According to the configurations of the Modified Embodiments 7 and 8, the number of reception circuits can be reduced comparing to the previous embodiments and, thus, the circuit configuration will be simplified and its cost can be reduced as well.

Modified Embodiment 9

Figure 15C:
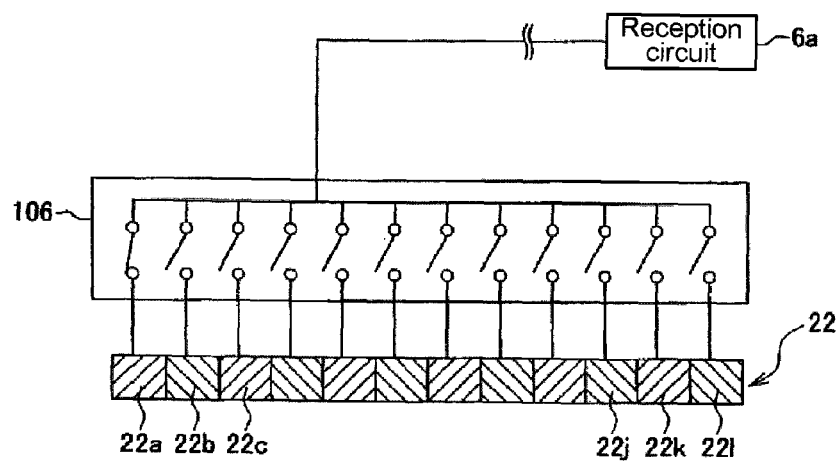

A change-over circuit, such as an analog switch, may be provided between the reception circuit and the arrayed transducer 22, and only some transducers among the twelve transducers 22*a*-22*l*, which are connected to the reception circuit through the change-over circuit may perform wave reception. For example, as shown in FIG. 15C, only one transducer among the twelve transducers 22*a*-22*l* may be connected to the reception circuit 6*a* through the change-over circuit 106.

The change-over circuit 106 switches over sequentially from one transducer to another, which is connected to the reception circuit, each time transmitting an ultrasonic wave. By transmitting the ultrasonic waves a total of twelve times, the received wave signals of the twelve transducers 22*a*-22*l* can be acquired. Note that an illustration of a circuit configuration of the transmission end is omitted in FIG. 15C. According to this configuration, the number of reception circuits can be reduced comparing to the previous embodiments and, thus, its cost can be reduced, while the received wave signals of the twelve transducers 22*a*-22*l* can be acquired similar to the previous embodiments.

Modified Embodiment 10

In the previous embodiments, the plurality of transducers 22*a*-22*l* constituting the arrayed transducer 22 perform both wave reception of the ultrasonic wave transmitted from the arrayed transducer 22 and wave reception of the ultrasonic wave transmitted from the transducer 21 dedicated to wave transmission. However, without limiting to this configuration, for example, four transducers 22*a*-22*d* on the side of the transducer 21 dedicated to wave transmission may perform only wave reception of the ultrasonic wave transmitted from the arrayed transducer 22, and four transducers 22*j*-22*l* on the opposite side from the transducer 21 dedicated to wave transmission may perform only wave reception of the ultrasonic wave transmitted from the transducer 21 dedicated to wave transmission, and further, four transducers 22*e*-22*h* of the central part may perform wave reception in both cases of wave transmission.

In this case, eight reception circuits may be provided, and a change-over circuit may be provided between the eight reception circuits and the arrayed transducer 22. In addition, the transducer that performs wave reception may be switched according to the transducer that transmits the ultrasonic wave (the transducer 21 dedicated to wave transmission or the arrayed transducer 22). According to this configuration, the number of reception circuits can be reduced comparing to the previous embodiments.

Modified Embodiment 11

Without providing the transducer 21 dedicated to wave transmission, an ultrasonic wave may be transmitted obliquely to the contacting face 2a by transmitting the ultrasonic wave whose phase may be controlled from the plurality of (for example, four) transducers at the end of the arrayed transducer 22.

According to this configuration, because the transducer 21 dedicated to wave transmission is unnecessary, the configuration of the ultrasonic transceiver 2 includes only the arrayed transducer 22 and, thus it can be simplified. Further, because the transducer 21 dedicated to wave transmission is not provided, the number of transducers that constitute the arrayed transducer 22 can be increased. Therefore, a range in which the bone shape can be detected will be wider. However, in this configuration, a plurality of transmission circuits is needed and the circuit configuration will be complicated with an increased cost. Thus, the previous embodiments may be more preferred for this regards.

Modified Embodiment 12

Figure 16A:
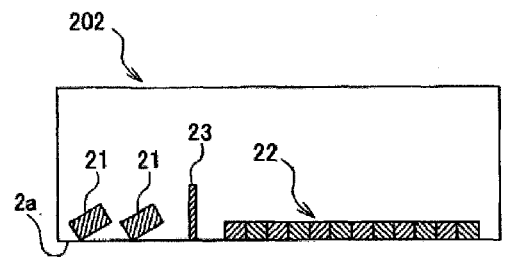
FIGS. 16A to 16C are views showing configurations of ultrasonic transceivers, where

In the ultrasonic transceiver 2 of the previous embodiments, although the number of transducers 21 dedicated to wave transmission is one, it may be an ultrasonic transducer 202 including two transducers 21 dedicated to wave transmission arranged in the same direction as the arrayed direction of the arrayed transducer 22 as shown in FIG. 16A, for example. In this configuration, a transducer that transmit an ultrasonic wave are selected from the two transducers 21 dedicated to wave transmission according to the thickness of the soft tissues 11 and/or the size of the curvature of the bone front surface 10a. According to this configuration, the arrayed transducer 22 can receive the leaky surface wave or the bone front-surface refracted wave more reliably.

Modified Embodiment 13

Figure 16B:
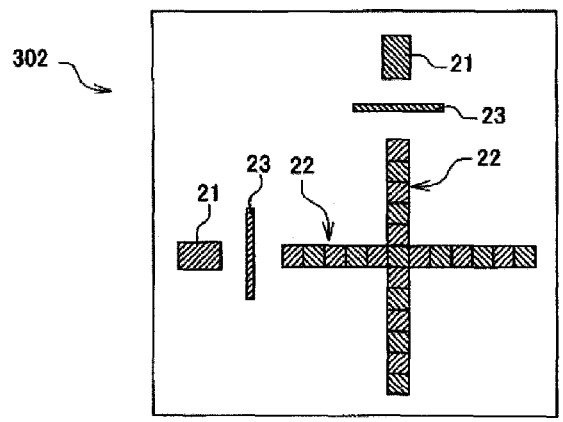

Similarly, for example, as shown in FIG. 16B, the ultrasonic transceiver 2 may be an ultrasonic transceiver 302 including two arrayed transducers 22 arranged perpendicularly to each other, and two transducers 21 dedicated to wave transmission arranged at the ends of the arranged direction of these two arrayed transducers 22. FIG. 16B is a plan view looking toward the contacting face 2a.

According to this configuration, without changing the orientation of the ultrasonic transceiver 302, a cross-sectional shape of the bone in the circumferential direction and a cross-sectional shape in the longitudinal direction can be detected, and the circumferential speed of sound and the longitudinal speed of sound can be derived as well. Therefore, the measuring time can be shortened.

Modified Embodiment 14

Figure 16C:
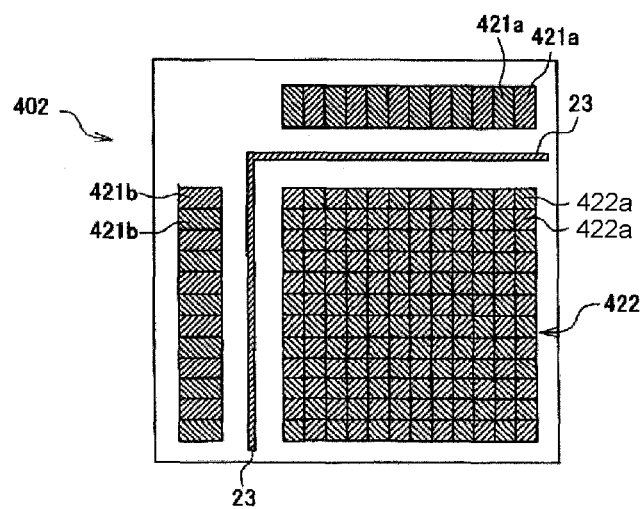

For example, the ultrasonic transceiver 2 may be an ultrasonic transceiver 402 including an arrayed transducer 422 having a plurality of transducers 422a arranged in a 6×6 matrix as shown in FIG. 16C, six transducers 421a dedicated to wave transmission arranged in the left-and-right direction in the upper part of the arrayed transducer 422 in FIG. 16C, six transducers 421b dedicated to wave transmission arranged in the up-and-down direction on the left-hand side of the arrayed transducer 422 in FIG. 16C.

According to this configuration, for example, from the right end of the matrix-arrayed transducer 422 in turn, using the six transducers 422a arranged in the up-and-down direction and the transducer 421a dedicated to wave transmission corresponding thereto, the bone shape is detected similar to the previous embodiments to derive the speed of sound in the bone using the detected bone shape. Accordingly, the three-dimensional shape of the bone 10 can be derived. In addition, the speed of sound of the ultrasonic wave that propagates in the up-and-down direction at the six locations in the left-and-right direction can be derived. Therefore, because the speed of sound in a certain direction can be measured at a plurality of locations, the speed of sound of the ultrasonic wave in the bone can be derived with more sufficient accuracy.

The speed of sound of the ultrasonic wave that propagates in the left-and-right direction can be derived at six locations in the up-and-down direction by deriving sequentially from the upper end of the arrayed transducer 422, speeds of sound using the six transducers 422a arranged in the left-and-right direction and the transducer 421b dedicated to wave transmission corresponding thereto arranged in the up-and-down direction.

Modified Embodiment 15

Figure 17:
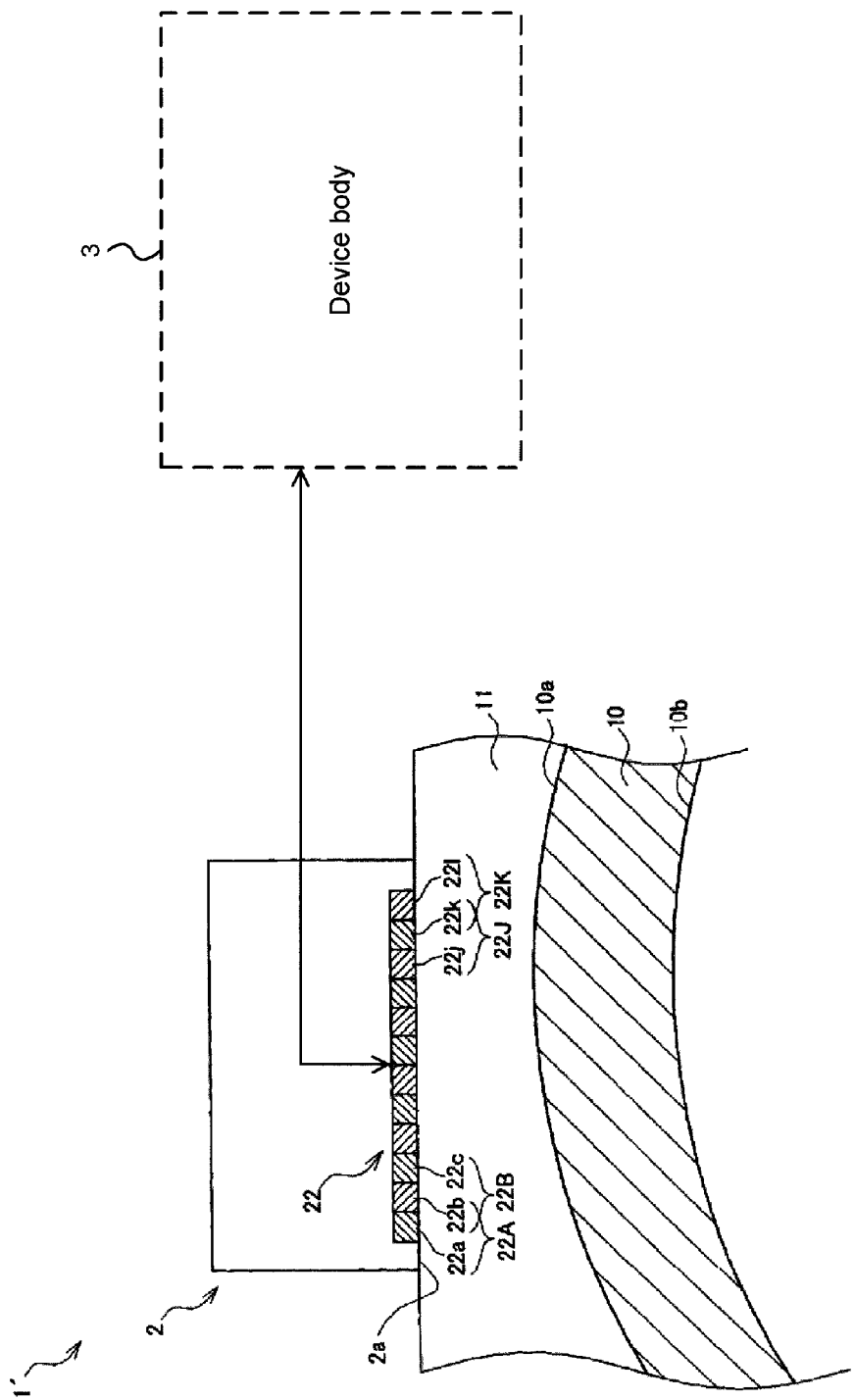
FIGS. 17 and 17B are a schematic diagram showing a configuration of a shape detection device according to Modified Embodiment 15.
Figure 17B:
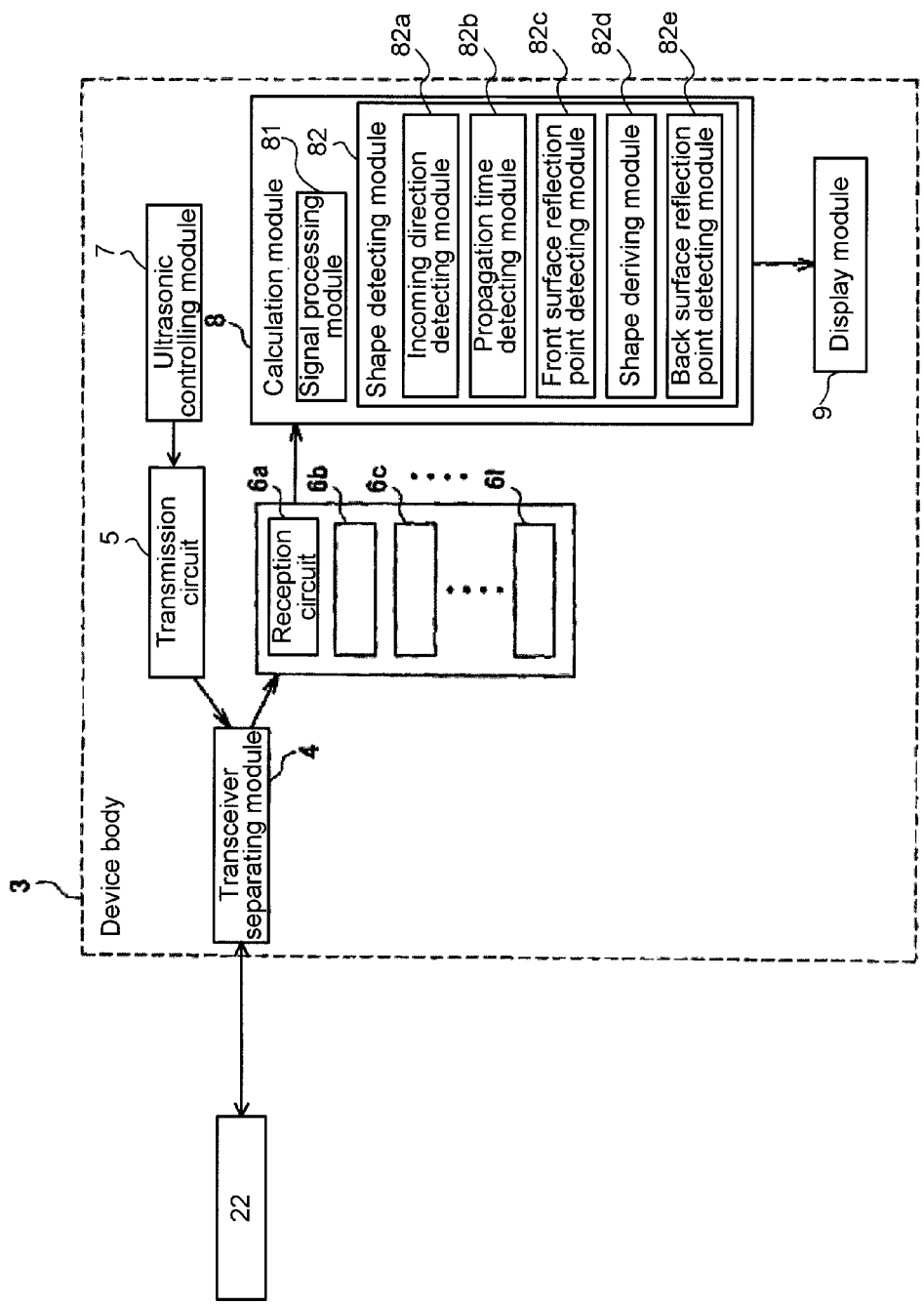

In the previous embodiments, the cases where the shape detection device according to the present invention is applied to a part of the bone strength diagnostic device are described as examples. However, the shape detection device according to the present invention may also be implemented independently from the bone strength diagnostic device and, thus, it may be applied to other applications. FIGS. 17 and 17B show a configuration example of a shape detection device 1' according to this modified embodiment. In this case, the object to be measured by the shape detection device 1' is not limited to a bone, and this device may be used to detect a shape of an inner circumferential face of a pipe or conduit, for example. Thus, a non-destructive test of pipe degradation can be conducted, for example. Further, even if the object to be measured is a bone, the shape detection device according to the present invention may also be applied to the bone strength diagnostic device that detects a thickness of a cortical bone to diagnose bone strength from the cortical bone thickness.

Modified Embodiment 16

Figure 18A:
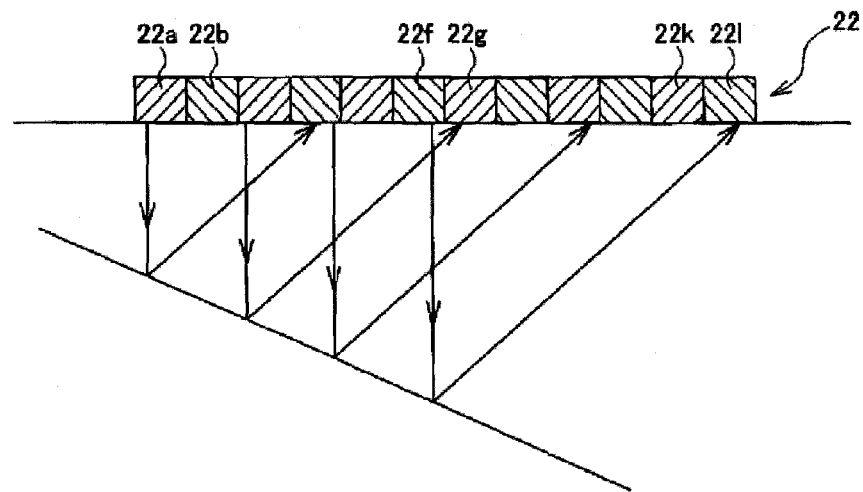
FIG. 18A is a schematic view showing a configuration of transducers according to Modified Embodiment 16.

The shape detection device according to the present invention may have a configuration including a plurality of transducers for wave transmission and a plurality of transducers for wave reception which are physically separated transducers from the transducers for wave transmission. For example, as shown in FIG. 18A, six transducers 22a-22f on one end side (left-hand side in FIG. 17) of the arrayed transducer 22 perform only wave transmission of an ultrasonic wave and six transducers 22g-22l on the other end side (right-hand side in FIG. 17) of the arrayed transducer 22 perform only wave reception of the ultrasonic wave. According to this configuration, even when a front surface (or a back surface) of the object to be measured inclines greatly to the contacting face 2a (see FIG. 17), reflected waves on the front surface (or reflected waves from the back surface) can be received. Note that two transducers 22f and 22g at the center may be configured to perform both wave transmission and wave reception, for example.

Modified Embodiment 17

Figure 18B:
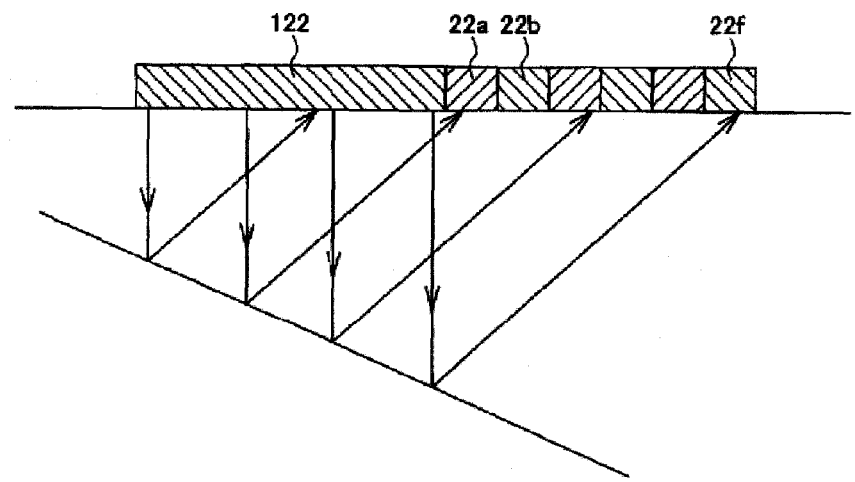
FIG. 18B is a schematic view showing a configuration of the transducers according to Modified Embodiment 17.

As shown in FIG. 18B, the shape detection device according to the present invention may be configured to transmit an ultrasonic wave from a single transducer 122 having a large oscillating surface for wave transmission to the target object, and receive the reflected wave from the object to be measured by the plurality of transducers 22a-22f for wave reception. The large transducer 122 may be 10 to 100 mm in its length, for example, in the left-and-right direction in FIG. 18B. In this case, the center frequency of the ultrasonic wave transmitted from the transducer 122 may be 1 to 10 MHz, for example. The ultrasonic wave transmitted from the transducer 122 propagates as a plane wave. According to this configuration, similar to Modified Embodiment 16, even if the front surface (or the back surface) of the object to be measured is inclined, reflected waves can still be received by a plurality of transducers for wave reception.

Modified Embodiment 18

Figure 19A:
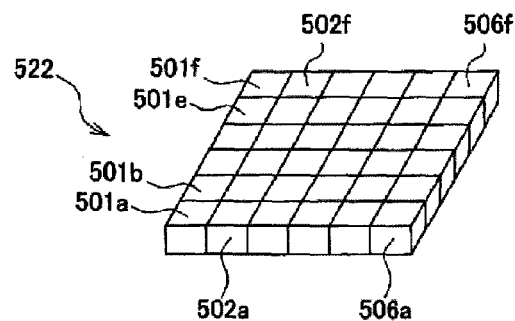
FIGS. 19A to 19C are views showing configurations of transducers, where

The shape detection device of this embodiment includes, instead of the arrayed transducer 22, the incoming direction detecting module 82a, and the propagation time detecting module 82b of the previous embodiments, as shown in FIG. 19A, an arrayed transducer 522 having a plurality of transducers arranged in a 6×6 matrix, for example, as well as an incoming direction detecting module 82a and a propagation time detecting module 82b as explained below. Hereinafter, a method of detecting a front-surface shape of the target object will be explained first.

First, ultrasonic waves of the same phase are simultaneously transmitted from all the transducers that constitute the arrayed transducer 522, and front-surface reflected waves on the front surface of the target object are then received by all the transducers that constitute the arrayed transducer 522. The incoming direction detecting module 82a determines a plurality of transducer groups 510 where each transducer group 510 is constituted with three proximate wave-reception transducers that are located in two perpendicularly intersecting rows (for example, 501a, 501b, and 502a in FIG. 19B) among the plurality of transducers (501a-501f, 502a-502f, . . . , and 506a-506f as shown in FIG. 19A) that constitute the arrayed transducer 522.

Figure 19B:
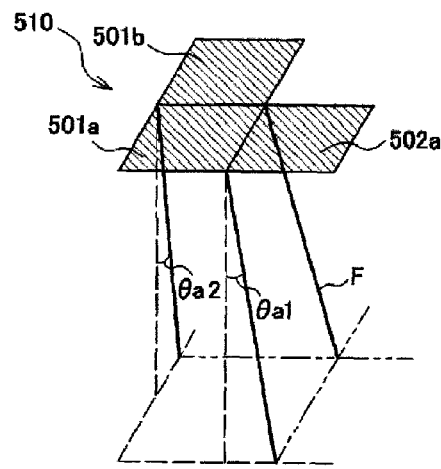

Using a time difference between timings at which the two transducers 501a and 502a arranged in a line in the left-and-right direction in FIG. 19B (that is, arranged in the row in the left-and-right direction) receive the front-surface reflected wave, respectively, an incoming angle θa1 (first incoming angle) of the front-surface reflected wave on a plane extending in the left-and-right direction is detected similar to the previous embodiments where the incoming angle θa is detected.

In addition, similarly regarding in the up-and-down direction, based on a time difference between the wave-reception timings of the front-surface reflected waves by two transducers 501a and 501b arranged in a line in the up-and-down direction in FIG. 19B (that is, arranged in the row in the up-and-down direction), an incoming angle θa2 (second incoming angle) of the front-surface reflected wave in a plane extending in the up-and-down direction is detected.

As shown in FIG. 19B, an incoming direction (a direction of an arrow F in FIG. 19B) of the front-surface reflected wave with respect to the transducer group 510 having three transducers 501a, 501b, and 502c is detected using the incoming angles θa1 and θa2. Regarding other transducer groups 510, incoming directions are detected similarly.

Next, the propagation time detecting module 82b detects a propagation time Ta of the front-surface reflected wave that reaches each transducer group 510 using the received wave signals of the front-surface reflected waves of three transducers (e.g., 501a, 501b, and 502a) constituting each transducer group 510. Although an average value of the propagation times of the front-surface reflected waves received by the three transducers is used in this embodiment for calculation of the propagation time Ta, an average value of the propagation times of the front-surface reflected waves received by two transducers among the three transducers may be used as well. Further, the propagation time of the front-surface reflected wave received by one of the three transducers may be used as the propagation time Ta as it is.

The front-surface reflection point detecting module 82c detects reflection points on the front surface of the target object similar to the previous embodiments using the incoming direction F and the propagation time Ta of the front-surface reflected wave that reaches each transducer group 510 which are detected by the incoming direction detecting module 82a and the propagation time detecting module 82b. In this embodiment, the shape deriving module 82 derives a three-dimensional shape of the front surface of the target object by using the plurality of detected reflection points.

According to this configuration, the incoming direction of the front-surface reflected wave to each transducer group can be detected three-dimensionally. Therefore, even if the shape of the front surface of the target object is a three-dimensional shape, such as a spherical surface, the shape can be detected in the three dimensions.

Modified Embodiment 19

Figure 19C:
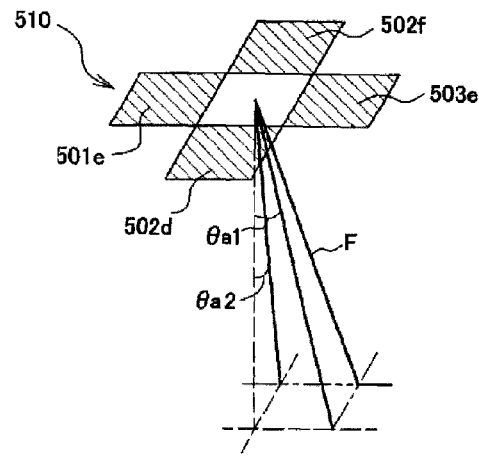

As shown in FIG. 19C, the front surface shape of the target object may be detected with a similar procedure to the previous embodiments, in which four proximate transducers (for example, 501e, 502d, 502f, and 503e) that are arranged in two rows intersecting perpendicularly to each other are selected as one set of the transducer group 510 among the plurality of wave-reception transducers that constitute the arrayed transducer 522, resulting in similar functions and effects to the configuration at the time of selecting three transducers as described above.

Modified Embodiment 20

If the object to be measured is constituted with a plurality of layers, a shape detection device of this embodiment may detect not only the shapes of the front surface and the back surface of the target object, which are the outermost layers, but the shape of the internal layer(s). Hereinafter, an example will be explained where a shape of a back surface 600c of an intermediate layer 602 is detected where the a target object 600 in cistituted with two layers as shown in FIG. 20 and the intermediate layer 602 is a second layer (hereinafter, simply referred to as the second layer) from the front outermost layer 601.

The incoming direction detecting module 82a calculates by a similar method to the previous embodiments an incoming angle θd of a reflected wave 614 from the back surface 600c of the second layer 602 reaching the transducer group 22A. Next, the back-surface reflection point detecting module 82e calculates by a similar method to the previous embodiments an angle of refractional and an angle of incidence α2 of the reflected wave 614 at a front surface 600a of the outermost layer 601 by using a front surface line Ia of the outermost layer 601 derived in advance. After that, using a back surface line Ib of the outermost layer 601 derived in advance, an angle of refraction α3 and a angle of incidence α4 of the reflected wave 614 at a back surface 600b of the outermost layer 601 (equivalent to the front surface of the second layer 602 as well) are calculated to derive a propagating direction of the reflected wave 614 in the second layer 602 (z-axis in FIG. 20).

Figure 20:
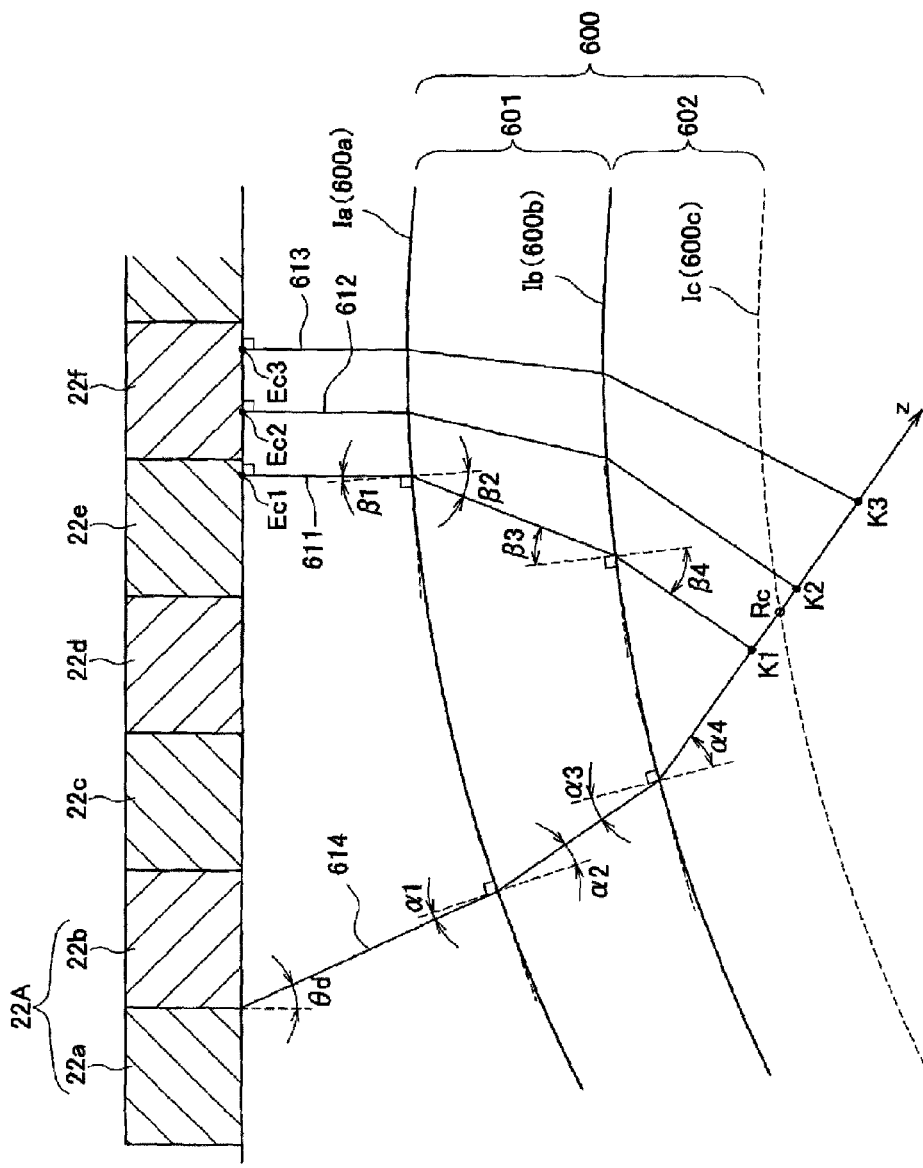
FIG. 20 is a schematic view for illustrating a method of detecting reflection points according to Modified Embodiment 20.

In addition, an angle of incidence β1 and an angle of refraction β2 of an incident wave 611 transmitted from a point Ec1 in FIG. 20 at the front surface 600a of the outermost layer 601 are calculated by a similar method to the previous embodiments. After that, an angle of incidence β3 and an angle of refraction β4 of the incident wave 611 at the back surface 600b of the outermost layer 601 are calculated, and a propagating direction of the incident wave 611 in the second layer 602 is derived. Similarly, propagating directions in the second layer 602, of the incident waves 612 and 613 transmitted from points Ec2 and Ec3 in FIG. 20 are also derived, respectively. Then, intersecting points K1, K2, and K3 of the propagating directions of the incident waves 611-613 and the z-axis are detected, respectively, and by a similar method to the previous embodiments, a reflection point Rc on the back surface 600c of the second layer 602 is derived.

A similar procedure is carried out for each of other six transducer groups 22A-22K to detect six reflection points Rc. The shape deriving module 82d connects the detected seven reflection points Rc with a curve or a straight line to derive a back-surface line Ic of the second layer 602.

If the target object has three or more layers, the shapes of the back surfaces of the third layer, fourth layer, fifth layer and so forth can also be detected by sequentially deriving the shape of each layer starting from the outermost layer of the target object.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims, including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "approximately" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

What is claimed is:

1. A shape detection device, comprising:
  a wave-transmission module for simultaneously transmitting ultrasonic waves from a plurality of wave-transmission transducers to a target object;
  a wave-reception module for receiving with a plurality of wave-reception transducers front-surface reflected waves of the ultrasonic wave transmitted from the wave-transmission module, reflected on a front surface of the target object;
  an incoming direction detecting module for detecting an incoming direction of one of the front-surface reflected waves to each of a plurality of transducer groups using a time difference between timings at which two wave-reception transducers constituting each transducer group receive one of the front-surface reflected waves, each transducer group being constituted with two wave-reception transducers adjacent to each other among the plurality of wave-reception transducers;
  a propagation time detecting module for detecting a propagation time of one of the front-surface reflected waves that reaches each transducer group using a received wave signal of the front-surface reflected wave of at least one of the two wave-reception transducers constituting each transducer group;
  a front-surface reflection point detecting module for detecting a plurality of reflection points of the ultrasonic waves on the front surface of the target object based on the incoming direction and the propagation time of the front-surface reflected wave detected for each transducer group by using the incoming direction detecting module and the propagation time detecting module, respectively; and
  a shape deriving module for deriving a shape of the front surface of the target object using the plurality of the reflection points on the front surface of the target object detected by the front-surface reflection point detecting module for the plurality of the transducer groups.

2. The shape detection device of claim 1, wherein the plurality of wave-transmission transducers serve as the wave-reception transducers as well.

3. The shape detection device of claim 1 or 2, wherein the plurality of wave-transmission transducers and the plurality of wave-reception transducers are arranged in a single row.

4. The shape detection device of claim 3, wherein the center frequency of the ultrasonic wave transmitted from the wave-transmission transducer is 1 to 10 MHz, and a length in the arranged direction of the wave-transmission transducer is 10 to 100 mm.

5. The shape detection device of claim 1 or 2, wherein the plurality of wave-transmission transducers and the plurality of wave-reception transducers are arranged in a matrix.

6. The shape detection device of claim 5, wherein the incoming direction detecting module detects an incoming direction of the front-surface reflected waves using a first time difference between wave-reception timings of a first group of wave-reception transducers and a second time difference between wave-reception timings of a second group of wave-reception transducers, where the first and second groups of wave-reception transducers are constituted with three or four wave-reception transducers selected from the plurality of wave-reception transducers and are arranged in two intersecting rows, wherein the three or four wave-reception transducers are proximate to each other to constitute each transducer group;

wherein the incoming direction detecting module further detects an incoming direction of the front-surface reflected waves to each transducer group based on a first incoming direction and a second incoming direction;

wherein the propagation time detecting module detects a propagation time of the front-surface reflected waves that reach each transducer group using a received wave signal of the front-surface reflected wave of at least one of the three or four wave-reception transducers constituting each transducer group.

7. The shape detection device of claim 1, wherein the wave-reception module receives back-surface reflected waves, reflected on a back surface of the target object that reach the plurality of wave-reception transducers after the front-surface reflected waves;

wherein the incoming direction detecting module detects an incoming direction of one of the back-surface reflected waves to each of a plurality of transducer groups using a time difference between timings at which the two wave-reception transducers constituting each transducer group receive the back-surface reflected waves; and wherein the propagation time detecting module detects a propagation time of one of the back-surface reflected waves that reaches each transducer group using a received wave signal of the back-surface reflected wave of at least one of the two wave-reception transducers constituting each transducer group;

the shape detection device further comprising a back-surface reflection point detecting module for detecting a plurality of reflection points of the ultrasonic waves on the back surface of the target object based on the incoming direction and the propagation time of the back-surface reflected wave detected for each transducer group by the incoming direction detecting module and the propagation time detecting module, respectively, and the shape of the front surface of the target object derived by the shape deriving module;

wherein the shape deriving module derives a shape of the back surface of the target object using the plurality of the reflection points on the back surface of the target object detected by the back-surface reflection point detecting module for the plurality of the transducer groups.

8. A bone strength diagnostic device comprising the shape detection device of claim 7 where the target object is a bone, wherein the shape deriving module derives a thickness of the bone based on the derived shapes of the front surface and the back surface of the bone, the bone strength diagnostic device comprising a bone strength diagnostic module for diagnosing a bone strength based on the thickness of the bone.

9. A shape detection device, comprising:
a wave-transmission module for simultaneously transmitting ultrasonic waves from a plurality of wave-transmission transducers to a target object having a plurality of layers;
a wave-reception module for receiving, with a plurality of wave-reception transducers, reflected waves of the ultrasonic wave transmitted from the wave-transmission module on a front surface of the target object and a back surface of each layer of the target object;
an incoming direction detecting module for detecting incoming directions of the reflected waves on the front surface of the target object and the back surface of each layer to each of a plurality of transducer groups using a time difference between received wave signals of two wave-reception transducers constituting each transducer group, each transducer group being constituted with two wave-reception transducers adjacent to each other among the plurality of wave-reception transducers;
a propagation time detecting module for detecting the propagation time of each of the reflected waves that reaches each transducer group using the received wave signal of each reflected wave of at least one of the two wave-reception transducers constituting each transducer group;
an outermost-layer front-surface shape detecting module for detecting a plurality of reflection points of the ultrasonic waves on the front surface of the target object to derive a shape of the front surface of the target object based on the incoming direction and the propagation time of the reflected waves from the front surface of the target object detected for each transducer group by the incoming direction detecting module and the propagation time detecting module; and
a back-surface shape deriving module for deriving a shape of the back surface of each layer sequentially from the outermost layer of the target object based on the incoming direction and the propagation time of the reflected waves from the back surface of each layer detected for each transducer group by the incoming direction detecting module and the propagation time detecting module, and the shape of the front surface of the target object detected by the outermost-layer front-surface shape detecting module.

10. A shape detection method, comprising:
simultaneously transmitting ultrasonic waves from a plurality of wave-transmission transducers to a target object;
receiving with a plurality of wave-reception transducers front-surface reflected waves of the transmitted ultrasonic waves on a front surface of the target object;
detecting an incoming direction of one of the front-surface reflected waves to each of a plurality of transducer groups using a time difference between timings at which two wave-reception transducers constituting each transducer group receive the front-surface reflected waves, each transducer group being constituted with two wave-reception transducers adjacent to each other among the plurality of wave-reception transducers;
detecting a propagation time of the front-surface reflected waves that reach each transducer group using a received wave signal of the front-surface reflected wave of at least one of the two wave-reception transducers constituting each transducer group;
detecting a plurality of reflection points of the ultrasonic waves on the front surface of the target object based on the incoming direction and the propagation time of the front-surface reflected waves detected for each transducer group; and
deriving a shape of the front surface of the target object using the plurality of the reflection points on the front surface of the target object detected for the plurality of the transducer groups.

11. The shape detection method of claim 10, wherein the receiving front-surface reflected waves includes receiving back-surface reflected waves on a back surface of the target object that reach the plurality of wave-reception transducers after the front-surface reflected waves;

- wherein the detecting the incoming direction of the front-surface reflected waves includes detecting an incoming direction of the back-surface reflected waves to each transducer group using a time difference between timings at which the two wave-reception transducers constituting each transducer group receive the back-surface reflected waves; and
- wherein the detecting the propagation time of the front-surface reflected waves includes detecting a propagation time of the back-surface reflected waves that reach each transducer group using a received wave signal of the back-surface reflected wave of at least one of the two wave-reception transducers constituting each transducer group;
- the method further comprising detecting a plurality of reflection points of the ultrasonic waves on the back surface of the target object based on the incoming direction and the propagation time of the back-surface reflected waves detected for each transducer group, and the derived shape of the front surface of the target object;
- wherein the deriving the shape of the front surface includes deriving a shape of the back surface of the target object using the plurality of the reflection points on the back surface of the target object detected for the plurality of transducer groups.

* * * * *